US011583575B2

(12) United States Patent
Klein et al.

(10) Patent No.: US 11,583,575 B2
(45) Date of Patent: Feb. 21, 2023

(54) MHC-BOUND PEPTIDE ARRAYS AND METHODS OF USE THEREOF

(71) Applicants: Roche Sequencing Solutions, Inc., Pleasanton, CA (US); Hoffmann-La Roche Inc., Little Falls, NJ (US)

(72) Inventors: Christian Klein, Bonstetten (CH); Hanying Li, Madison, WI (US); Victor Lyamichev, Madison, WI (US); Ekkehard Moessner, Kreuzlingen (CH); Jigar Patel, Verona, WI (US)

(73) Assignees: Roche Sequencing Solutions, Inc., Pleasanton, CA (US); Hoffmann-La Roche Inc., Little Falls, NJ (US)

( * ) Notice: Subject to any disclaimer, the term of this patent is extended or adjusted under 35 U.S.C. 154(b) by 1078 days.

(21) Appl. No.: 15/695,536

(22) Filed: Sep. 5, 2017

(65) Prior Publication Data

US 2018/0356424 A1    Dec. 13, 2018

Related U.S. Application Data

(60) Provisional application No. 62/384,088, filed on Sep. 6, 2016.

(51) Int. Cl.
| | |
|---|---|
| *C07K 14/70* | (2006.01) |
| *A61K 39/00* | (2006.01) |
| *A61K 39/12* | (2006.01) |
| *A61P 31/20* | (2006.01) |
| *A61P 35/00* | (2006.01) |
| *C07K 14/74* | (2006.01) |
| *C07K 17/06* | (2006.01) |
| *C07K 19/00* | (2006.01) |
| *G01N 33/543* | (2006.01) |
| *G01N 33/544* | (2006.01) |
| *G01N 33/569* | (2006.01) |
| *G01N 33/68* | (2006.01) |

(52) U.S. Cl.
CPC .. *A61K 39/0011* (2013.01); *A61K 39/001153* (2018.08); *A61K 39/001186* (2018.08); *A61K 39/001188* (2018.08); *A61K 39/12* (2013.01); *A61P 31/20* (2018.01); *A61P 35/00* (2018.01); *C07K 14/70539* (2013.01); *C07K 17/06* (2013.01); *C07K 19/00* (2013.01); *G01N 33/544* (2013.01); *G01N 33/54313* (2013.01); *G01N 33/56977* (2013.01); *G01N 33/6842* (2013.01); *G01N 33/6845* (2013.01); *A61K 2039/64* (2013.01); *C07K 2319/31* (2013.01); *C07K 2319/70* (2013.01); *C12N 2710/24134* (2013.01); *G01N 2333/7051* (2013.01); *G01N 2333/70539* (2013.01); *G01N 2500/04* (2013.01); *G01N 2500/20* (2013.01); *G01N 2570/00* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,635,363 A | 6/1997 | Altman et al. | |
| 5,869,270 A | 2/1999 | Rhode et al. | |
| 6,375,903 B1 | 4/2002 | Cerrina et al. | |
| 7,022,483 B1 | 4/2006 | Albani | |
| 7,074,904 B2 | 7/2006 | Wong et al. | |
| 7,074,905 B2 | 7/2006 | Rhode et al. | |
| 7,902,121 B2 | 3/2011 | Chen et al. | |
| 7,994,096 B2 | 8/2011 | Kern et al. | |
| 8,030,477 B2 | 10/2011 | Cerrina et al. | |
| 2003/0013130 A1* | 1/2003 | Charych | B01J 19/0046 435/7.1 |
| 2004/0209295 A1 | 10/2004 | Schwabe et al. | |
| 2004/0248205 A1 | 12/2004 | Stern et al. | |
| 2005/0019843 A1 | 1/2005 | Chen et al. | |
| 2013/0029358 A1 | 1/2013 | Valmori et al. | |
| 2013/0245385 A1 | 9/2013 | Hildebrand et al. | |
| 2017/0192011 A1* | 7/2017 | Birnbaum | G01N 33/6845 |

FOREIGN PATENT DOCUMENTS

| | | |
|---|---|---|
| EP | 3 228 322 A1 | 10/2017 |
| JP | 2013-522276 A | 6/2013 |
| JP | 2015-509583 A | 3/2015 |
| WO | WO-95/27901 A1 | 10/1995 |
| WO | WO 02/072631 A2 | 9/2002 |
| WO | WO-2004/006951 A1 | 1/2004 |
| WO | WO-2004/094458 A2 | 11/2004 |
| WO | WO-2005/010026 A2 | 2/2005 |
| WO | WO-2008/151146 A2 | 12/2008 |
| WO | WO-2010/038027 A1 | 4/2010 |
| WO | WO-2011/113872 A1 | 9/2011 |
| WO | WO-2013/119845 A1 | 8/2013 |

OTHER PUBLICATIONS

Northen et al (Advanced Materials 20:4691-7) (Year: 2008).*
Garboczi et al (PNAS 89:3429-33) (Year: 1992).*
International Preliminary Report on Patentability in International Patent Application No. PCT/EP2017/072165 dated Mar. 12, 2019 (7 pages).

(Continued)

*Primary Examiner* — Christopher M Gross
(74) *Attorney, Agent, or Firm* — Foley & Lardner LLP

(57) ABSTRACT

The disclosure provides compositions comprising at least one assembly comprising a peptide and a major histocompatibility complex (MHC), wherein the peptide is an integral component of the MHC, wherein the peptide is attached to a surface at its C-terminus through a linker and wherein the peptide is synthesized on the surface. In certain embodiments, the compositions comprise a plurality of assemblies in a spatially-ordered array. The disclosure provides methods for making and using these compositions.

23 Claims, 10 Drawing Sheets
(10 of 10 Drawing Sheet(s) Filed in Color)
Specification includes a Sequence Listing.

(56) References Cited

OTHER PUBLICATIONS

International Search Report and Written Opinion in International Patent Application No. PCT/EP2017/072165 dated Jan. 12, 2017 (11 pages).
Communication pursuant to Article 94(3) EPC in EP Patent Application No. 17768392.7 dated Feb. 21, 2020, 6 pages.
John D. Altman, et al. "Phenotypic Analysis of Antigen-Specific T Lymphocytes", Science, (1996), pp. 94-96.
Cox, et al., "Identification of a Peptide Recognized by Five Melanoma-Specific Human Cytotoxic T Cell Lines", Science, vol. 264, (Apr. 29, 1994), p. 716-719.
Suzanne E. Brooks, et al., "Application of the pMHC Array to Characterise Tumour Antigen Specific T Cell Populations in Leukaemia Patients at Disease Diagnosis", PLoS One 10.1371/journal.pone. 0140483 (Oct. 23, 2015), pp. 1-19.
Beatriz M. Carreno, et al., "A dendritic cell vaccine increases the breadth and diversity of melanoma neoantigen-specific T. cells", Science, vol. 348, Issue 6236, (2015), pp. 803-809.
Pratip K. Chattopadhyay, et al., "Quantum dot semiconductor nanocrystals for immunophenotyping by polychromatic flow cytometry", Nature Med. , vol. 12, No. 8, (Aug. 2006), pp. 972-977.
Chen, et al, "A testicular antigen aberrantly expressed in human cancers detected by autologous antibody screening", Proc Nat'l Acad Sci. 94 (1997), pp. 1914-1918.
Chen, et al., "Marked Differences in Human Melanoma Antigen-Specific T Cell Responsiveness after Vaccination Using a Functional Microarray", PLoS Medicine, vol. 2, Issue 10, (2005), pp. 1018-1030.
Tao Dao, et al., "Targeting the Intracellular WT1 Oncogene Product with a Therapeutic Human Antibody", www.ScienceTranslationMedicine.org, vol. 5, Issue 176 176ra33, (Mar. 13, 2013), pp. 1-13.
G. Deviren, et al., "Detection of antigen-specific T cells on p/MHC microarrays", J Mol Recognit 20 DOI: 10.1003/jmr.805, (2007), pp. 32-38.
Fei Duan, et al., "Genomic and bioinformatics profiling of mutational neoepitopes reveals new rules to predict anticancer immunogenicity", J. Exp. Med. (2014), vol. 211, No. 11, pp. 2231-2248.
Kirsten Falk, et al., "Allele-specific motifs revealed by sequencing of self-peptides eluted from MHC molecules", Nature, 351 (1991), pp. 290-296.
D.N. Garboczi, et al., "HLA-A2-peptide complexes: Refolding and crystallization of molecules expressed in Escherichia coli and completexed with single antigenic peptides", Proc natl. Acad Sci, USA, vol. 89, pp. 3429-3433, Apr. 1992.
Hadrup, et al., "Parallel detection of antigen-specific T-cell responses by multidimensional encoding of MHC multimers", Nat America, Inc., DOI:10.1038/NMETH.1345 (2009), pp. 520-528.
Hadrup, et al., "High-Throughput T-Cell Epitope Discovery Through MHC Peptide Exchange", Methods in Molecular Biology, vol. 524, DOI: 10.1007/978-1-59745-450-6_28, (2009), pp. 383-405.
Michael Holcapek, et al., "Recent developments in liquid chromatography-mass spectrometry and related techinques", J Chromatography A 1259 (2012), pp. 3-15.
Karuna P. Karunakaran, et al., "Immunoproteomic Discovery of Novel T Cell Antigens from the Obligate Intracellular Pathogen Chlamydia", The Journal of Immunology, 180 (2008), pp. 2459-2465.
Yutaka Kawakami, et al., "Cloning of the gene coding for a shared human melanoma antigen recognized by autologous T cells infiltrating into tumor", Proc. Natl Acad Sci, 91 (1994), pp. 3515-3519.
Kern, et al. "Analysis of CD8 T cell reactivity to cytomegalovirus using protein-spanning pools of overlapping pentadecapeptides", Eur. J. Immunol, (2000) 30: pp. 1676-1682.
Kwong GA, et al., "Modular Nucleic Acid Asembled p/MHC Microarrays for Multiplexed Sorting of Antigen-Specific T Cells", J AM Chem Soc 131, (2009), pp. 9695-9703.
Kyte, et al., "A Simple Method for Displaying the Hydropathic Character of a Protein", J. Mol. Biol, 157: (1982) pp. 105-132.
Mohammed, et al., "Phosphorylation-dependent interaction between antigenic peptides and MHC class I: a molecular basis for the presentation of transformed self", Nature Immunol, vol. 9, (2008), pp. 1236-1243.
Newell, et al., Combinatorial tetramer staining and mass cytometry analysis facilitate T-cell epitope mapping and characterization, Nat Biotechnol, 31 (2013), pp. 623-629.
Stephen P. Perfetto, et al., "Seventeen-colour flow cytometry unravelling the immune system", Nat Rev Immunol, vol. 4 (2004), pp. 648-655.
Michael L. Silver, et al., Reconstitution by MHC-restricted peptides of HLA-A2 heavy chain with $\beta$2-microglobulin, in vitro, Nature, vol. 350, (Apr. 18, 1991), pp. 619-622.
Yoav Soen, et al., "Detection and Characterization of Cellular Immune Responses Using Peptide-MHC Microarrays", PLOS Biology, vol. 1, Issue 3, pp. 429-438.
Stone, et al., "HLA-restricted epitope identification and detection of functional T cell responses by using MHC-peptide and costimulatory microarrays", Proc Natl Acad Sci USA 102 (2005), pp. 3744-3749.
Tatiana A. Tatusova, et al., "BLAST 2 Sequences, a new tool for comparing proteins ad nucleotid sequences", FEMS Microbiology Letters 174, (1999), pp. 247-250.
Toebes, et al., "Design and use of conditional MHC class I lignads", Nat Med 12 (2006), pp. 246-251.
P. Van Der Bruggen, et al., "A Gene Encoding an Antigen Recognized by Cytolytic T. Lymphocytes on a Human Melanoma", Science, 254 (1991), pp. 1643-1647.
Simon D. van Haren, et al., "HLA-DR-presented Peptide Repertoires Derived from Human Monocyte-derived Dendritic Cells Pulsed With Blood Coagulation Factor VIII", Molecular & Cellular Proteomics 10.6, (2011) 10.1074/mcp.M110.002246, pp. 1-12.
Weiguo Zhang, et al., "Crystal structure of the major histocompatibility complex class I H-2K$^b$ molecule containing a single viral peptide: Implications for peptide binding and T-cell receptor recognition", Proc Natl Acad Sci, vol. 89, pp. 8403-8407, Sep. 1992.
Albert L. Lehninger, "Biochemistry: The Molecular Basis of Cell Structure and Function", Worth Publishers, Second Edition, (1975), pp. 71-77.
Anjanappa, R., et al., "Structures of peptide-free and partially loaded MHC class I molecules reveal mechanisms of peptide selection," Nature Communications, 11:1314 (2020) (11 pages).
Cresswell, P., "Intracellular Surveillance: Controlling the Assembly of MHC Class I-Peptide Complexes," Traffic, Munksgaard Intl. Pub., 1:301-305 (2000) (5 pages).
Office Action mailed in JP 2019-512661 dated Sep. 2, 2021 (with English translation) (6 pages).
Raghavan, M., et al., "MHC class I assembly: out and about," Trends Immunol., 29(9):436-443 (2008) (15 pages).
Reich, Z., et al., "Stability of empty and peptide-loaded class II major histocompatibility complex molecules at neutral and endosomal pH: Comparison to class I proteins," Proc. Natl. Acad. Sci. USA, Immunol., 94:2495-2500 (1997) (6 pages).
Office Action on JP 2019-512661 dated Mar. 11, 2022, 13 pages including English translation.
Office Action and Search Report on CN 201780066774.6 dated Jun. 2, 2022, including English Translation (21 Pages).
Bertrand Meresse, et al., Celiac Disease: An Immunological Jigsaw, Immunity, vol. 36, Issue 6, pp. 907-919, 2012.

* cited by examiner

FIG. 6

HLA-A2 loading specificity for Vaccinia Virus Peptide: LMYDIINSV

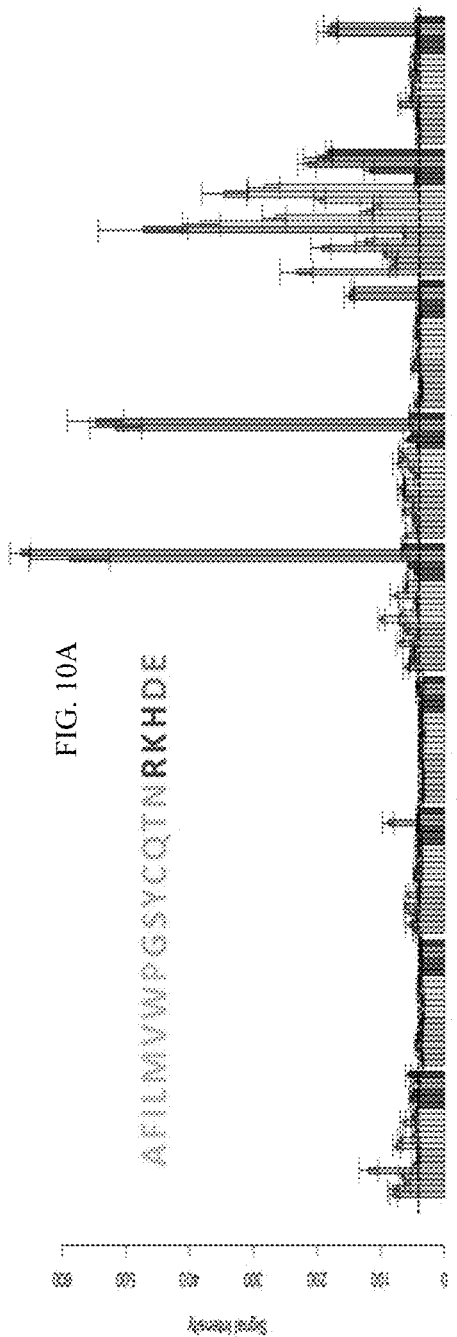
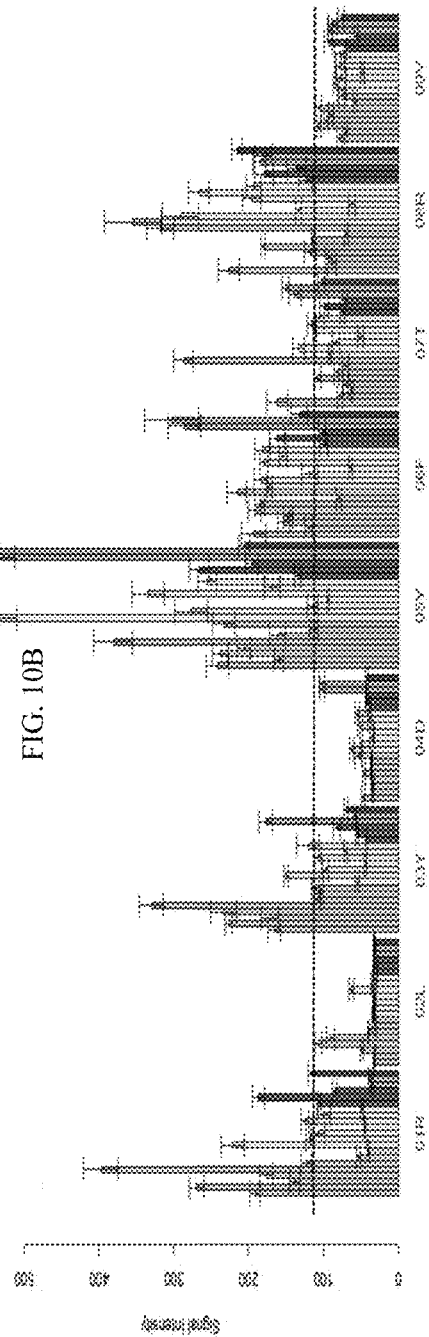
FIG. 10A
FIG. 10B

SEQUENCE LISTING

<160> NUMBER OF SEQ ID NOS: 10

<210> SEQ ID NO 1
<211> LENGTH: 276
<212> TYPE: PRT
<213> ORGANISM: Homo sapiens

<400> SEQUENCE: 1

```
Met Gly Ser His Ser Met Arg Tyr Phe Tyr Thr Ser Val Ser Arg Pro
1               5                   10                  15

Gly Arg Gly Glu Pro Arg Phe Ile Ala Val Gly Tyr Val Asp Asp Thr
            20                  25                  30

Gln Phe Val Arg Phe Asp Ser Asp Ala Ala Ser Gln Arg Met Glu Pro
        35                  40                  45

Arg Ala Pro Trp Ile Glu Gln Glu Gly Pro Glu Tyr Trp Asp Gln Glu
    50                  55                  60

Thr Arg Asn Val Lys Ala Gln Ser Gln Thr Asp Arg Val Asp Leu Gly
65                  70                  75                  80

Thr Leu Arg Gly Tyr Tyr Asn Gln Ser Glu Asp Gly Ser His Thr Ile
                85                  90                  95

Gln Ile Met Tyr Gly Cys Asp Val Gly Pro Asp Gly Arg Phe Leu Arg
            100                 105                 110

Gly Tyr Arg Gln Asp Ala Tyr Asp Gly Lys Asp Tyr Ile Ala Leu Asn
        115                 120                 125

Glu Asp Leu Arg Ser Trp Thr Ala Ala Asp Met Ala Ala Gln Ile Thr
    130                 135                 140

Lys Arg Lys Trp Glu Ala Ala His Ala Ala Glu Gln Gln Arg Ala Tyr
145                 150                 155                 160
```

```
Leu Glu Gly Arg Cys Val Glu Trp Leu Arg Arg Tyr Leu Glu Asn Gly
                165                 170                 175

Lys Glu Thr Leu Gln Arg Thr Asp Pro Pro Lys Thr His Met Thr His
            180                 185                 190

His Pro Ile Ser Asp His Glu Ala Thr Leu Arg Cys Trp Ala Leu Gly
        195                 200                 205

Phe Tyr Pro Ala Glu Ile Thr Leu Thr Trp Gln Arg Asp Gly Glu Asp
    210                 215                 220

Gln Thr Gln Asp Thr Glu Leu Val Glu Thr Arg Pro Ala Gly Asp Gly
225                 230                 235                 240

Thr Phe Gln Lys Trp Ala Ala Val Val Val Pro Ser Gly Glu Glu Gln
                245                 250                 255

Arg Tyr Thr Cys His Val Gln His Glu Gly Leu Pro Lys Pro Leu Thr
                260                 265                 270

Leu Arg Trp Glu
            275

<210> SEQ ID NO 2
<211> LENGTH: 275
<212> TYPE: PRT
<213> ORGANISM: Homo sapiens

<400> SEQUENCE: 2

Gly Ser His Ser Met Arg Tyr Phe Tyr Thr Ser Val Ser Arg Pro Gly
1               5                   10                  15

Arg Gly Glu Pro Arg Phe Ile Ser Val Gly Tyr Val Asp Asp Thr Gln
            20                  25                  30

Phe Val Arg Phe Asp Ser Asp Ala Ala Ser Pro Arg Glu Glu Pro Arg
        35                  40                  45

Ala Pro Trp Ile Glu Gln Glu Gly Pro Glu Tyr Trp Asp Arg Asn Thr
    50                  55                  60

Gln Ile Tyr Lys Ala Gln Ala Gln Thr Asp Arg Glu Ser Leu Arg Asn
65                  70                  75                  80

Leu Arg Gly Tyr Tyr Asn Gln Ser Glu Ala Gly Ser His Thr Leu Gln
                85                  90                  95

Ser Met Tyr Gly Cys Asp Val Gly Pro Asp Gly Arg Leu Leu Arg Gly
            100                 105                 110

His Asp Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Glu Ala Glu Gln Arg Arg Ala Tyr Leu
145                 150                 155                 160

Glu Gly Glu Cys Val Glu Trp Leu Arg Arg Tyr Leu Glu Asn Gly Lys
                165                 170                 175

Asp Lys Leu Glu Arg Ala Asp Pro Pro Lys Thr His Val Thr His His
            180                 185                 190

Pro Ile Ser Asp His Glu Ala Thr Leu Arg Cys Trp Ala Leu Gly Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Arg Thr
225                 230                 235                 240

Phe Gln Lys Trp Ala Ala Val Val Val Pro Ser Gly Glu Glu Gln Arg
                245                 250                 255
```

```
Tyr Thr Cys His Val Gln His Glu Gly Leu Pro Lys Pro Leu Thr Leu
            260                 265                 270

Arg Trp Glu
        275

<210> SEQ ID NO 3
<211> LENGTH: 274
<212> TYPE: PRT
<213> ORGANISM: Homo sapiens

<400> SEQUENCE: 3

Ser His Ser Met Arg Tyr Phe Asp Thr Ala Val Ser Arg Pro Gly Arg
1               5                   10                  15

Gly Glu Pro Arg Phe Ile Ser Val Gly Tyr Val Asp Asp Thr Gln Phe
            20                  25                  30

Val Arg Phe Asp Ser Asp Ala Ala Ser Pro Arg Gly Glu Pro Arg Ala
        35                  40                  45

Pro Trp Val Glu Gln Glu Gly Pro Glu Tyr Trp Asp Arg Glu Thr Gln
50                  55                  60

Lys Tyr Lys Arg Gln Ala Gln Ala Asp Arg Val Ser Leu Arg Asn Leu
65                  70                  75                  80

Arg Gly Tyr Tyr Asn Gln Ser Glu Asp Gly Ser His Thr Leu Gln Arg
                85                  90                  95

Met Ser Gly Cys Asp Leu Gly Pro Asp Gly Arg Leu Leu Arg Gly Tyr
            100                 105                 110

Asp Gln Ser Ala Tyr Asp Gly Lys Asp Tyr Ile Ala Leu Asn Glu Asp
        115                 120                 125

Leu Arg Ser Trp Thr Ala Ala Asp Thr Ala Ala Gln Ile Thr Gln Arg
130                 135                 140

Lys Leu Glu Ala Ala Arg Ala Ala Glu Gln Leu Arg Ala Tyr Leu Glu
145                 150                 155                 160

Gly Thr Cys Val Glu Trp Leu Arg Arg Tyr Leu Glu Asn Gly Lys Glu
                165                 170                 175

Thr Leu Gln Arg Ala Glu Pro Pro Lys Thr His Val Thr His His Pro
            180                 185                 190

Leu Ser Asp His Glu Ala Thr Leu Arg Cys Trp Ala Leu Gly Phe Tyr
        195                 200                 205

Pro Ala Glu Ile Thr Leu Thr Trp Gln Arg Asp Gly Glu Asp Gln Thr
210                 215                 220

Gln Asp Thr Glu Leu Val Glu Thr Arg Pro Ala Gly Asp Gly Thr Phe
225                 230                 235                 240

Gln Lys Trp Ala Ala Val Val Val Pro Ser Gly Gln Glu Gln Arg Tyr
                245                 250                 255

Thr Cys His Met Gln His Glu Gly Leu Gln Glu Pro Leu Thr Leu Ser
            260                 265                 270

Trp Glu

<210> SEQ ID NO 4

<400> SEQUENCE: 4

000
```

```
<210> SEQ ID NO 5

<400> SEQUENCE: 5

000

<210> SEQ ID NO 6

<400> SEQUENCE: 6

000

<210> SEQ ID NO 7
<211> LENGTH: 9
<212> TYPE: PRT
<213> ORGANISM: Homo sapiens

<400> SEQUENCE: 7

Arg Met Phe Pro Asn Ala Pro Tyr Leu
1               5

<210> SEQ ID NO 8
<211> LENGTH: 9
<212> TYPE: PRT
<213> ORGANISM: Vaccinia virus

<400> SEQUENCE: 8

Leu Met Tyr Asp Ile Ile Asn Ser Val
1               5

<210> SEQ ID NO 9
<211> LENGTH: 9
<212> TYPE: PRT
<213> ORGANISM: Homo sapiens

<400> SEQUENCE: 9

Arg Val Pro Gly Val Ala Pro Thr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Leu Tyr Asp Tyr Phe Thr Arg Val
1               5
```

MHC-BOUND PEPTIDE ARRAYS AND METHODS OF USE THEREOF

RELATED APPLICATIONS

This application claims priority to, and the benefit of U.S. Provisional Application No. 62/384,088 filed on Sep. 6, 2016, the contents of which are incorporated herein by reference in their entirety.

FIELD OF THE DISCLOSURE

The disclosure is directed to molecular biology, synthetic biology, protein arrays, and immunology, as well as medical and research tools.

INCORPORATION BY REFERENCE OF SEQUENCE LISTING

The contents of the text file named "RMSI-009-001US_SL.txt" which was created on Aug. 18, 2017, and is 8,293 bytes in size, are hereby incorporated by reference in their entirety.

BACKGROUND

There has been a long-felt but unmet need in the art for a surface-bound peptide presented by properly assembled major histocompatibility complex (MHC) that can be synthesized in situ for in vitro analysis of the peptide in an accurate biological context. The disclosure provides a solution to this long-felt but unmet need.

SUMMARY

The disclosure provides an in vitro system for assaying interactions between a peptide presented by an assembled major histocompatibility complex (MHC) and an immune cell (e.g. a T-cell) to identify those peptides and cells that are biologically relevant in vivo. The compositions of the disclosure provide a unique ability to identify single peptides that are immunodominant in vivo by providing a surface with each peptide attached to the surface in a spatially ordered array. The spatial ordering of the peptides is made possible by synthesizing each peptide in situ on the surface.

The compositions of the disclosure have succeeded where not only others have made attempts and failed, but also against the prevailing opinions of the state of the art. For example, for those compositions comprising a class I MHC, the prevailing wisdom dictates that both the amino terminus (N-terminus) and the carboxy terminus (C-terminus) of the peptide must be free, unbound or untethered to properly assemble in the MHC.

Using the compositions of the disclosure, immunodominant peptides may be identified for any condition. Moreover, while the state of the art relies on computer algorithms to predict immunodominant peptides that may or may not be relevant in vivo. In contrast, the compositions of the disclosure have the ability to simultaneously analyze at least $10^6$ unique peptides to specifically identify those peptides that activate immune cells. Because the MHC on the surface precisely recapitulates the peptide-MHC assembly on the surface of the array as the peptide-MHC assembly would appear on the surface of a cell in vivo, the compositions of the disclosure identify peptides that are relevant in vivo, and, therefore, do not require further empirical verification, eliminating a slow and expensive step required by existing technologies. Because each of these peptides are spatially-ordered and their sequences are pre-determined, the sequences of the immunodominant peptides are immediately known, eliminating another slow and expensive step, the sequencing of relevant peptides, also required by existing technologies.

By analyzing peptide variants, the compositions of the disclosure may be used to identify the essential amino acids (also referred to as "anchor points") for the successful assembly of each peptide-MHC, regardless of class (e.g. MHC class I or II) and regardless of which leukocyte antigen contributes to the MHC (e.g. HLA-A, HLA-B, or HLA-C).

Specifically, the disclosure provides a composition comprising at least one assembly comprising a peptide and a major histocompatibility complex (MHC), wherein the peptide is an integral component of the MHC, wherein the peptide is attached to a surface at its C-terminus through a linker and wherein the peptide is synthesized on the surface. In certain embodiments, the at least one assembly is a plurality of assemblies.

The MHC may be encoded by a leukocyte antigen gene from any mammalian species, including, but not limited to human (i.e., a human leukocyte antigen (HLA) gene), primate (e.g., apes, monkeys, chimps, and bonobo), and mouse (i.e., a mouse leukocyte antigen (MLA) gene).

In certain embodiments of the compositions of the disclosure, the MHC is a class I MHC.

In certain embodiments of the compositions of the disclosure, wherein the MHC is a class I MHC, the α-chain of the MHC may be truncated. For example, in certain embodiments, the α-chain of the MHC does not include a transmembrane region or a cytoplasmic region. In certain embodiments, wherein the MHC is a class I MHC, the α-chain of the MHC does not include a hinge region. In certain embodiments wherein the MHC is a class I MHC, the α-chain of the MHC does not include a transmembrane region, a hinge region or a cytoplasmic region. In certain embodiments wherein the MHC is a class I MHC, the α-chain of the MHC comprises an $\alpha_1$ domain, an $\alpha_2$ domain and an $\alpha_3$ domain. In certain embodiments, wherein the MHC is a class I MHC, the α-chain of the MHC may be encoded by a sequence derived from an HLA gene selected from the group consisting of an HLA-A gene, an HLA-B gene, an HLA-C gene, an HLA-E gene, an HLA-F gene, an HLA-G gene, an HLA-K pseudogene and an HLA-L pseudogene. Alternatively, wherein the MHC is a class I MHC, the α-chain of the MHC may be encoded by a sequence derived from an HLA gene selected from the group consisting of an HLA-A gene, an HLA-B gene and an HLA-C gene. Alternatively, wherein the MHC is a class I MHC, the α-chain of the MHC may be encoded by sequence derived from an HLA-A gene.

In certain embodiments of the compositions of the disclosure, the MHC is a class I MHC. The α-chain of the MHC may be encoded by sequence derived from an HLA-A gene, and specifically, HLA-A*11:01. The amino acid sequence of HLA-A*11:01 may comprise or consist of:

(SEQ ID NO: 1)
MGSHSMRYFYTSVSRPGRGEPRFIAVGYVDDTQFVRFDSDAASQRMEPR

APWIEQEGPEYWDQETRNVKAQSQTDRVDLGTLRGYYNQSEDGSHTIQI

MYGCDVGPDGRFLRGYRQDAYDGKDYIALNEDLRSWTAADMAAQITKRK

WEAAHAAEQQRAYLEGRCVEWLRRYLENGKETLQRTDPPKTHMTHHPIS

-continued
DHEATLRCWALGFYPAEITLTWQRDGEDQTQDTELVETRPAGDGTFQKW

AAVVVPSGEEQRYTCHVQHEGLPKPLTLRWE.

In certain embodiments of the compositions of the disclosure, the MHC is a class I MHC. The α-chain of the MHC may be encoded by sequence derived from an HLA-B gene, and specifically, HLA-B*07:02. The amino acid sequence of HLA-B*07:02 may comprise or consist of:

(SEQ ID NO: 2)
GSHSMRYFYTSVSRPGRGEPRFISVGYVDDTQFVRFDSDAASPREEPRA

PWIEQEGPEYWDRNTQIYKAQAQTDRESLRNLRGYYNQSEAGSHTLQSM

YGCDVGPDGRLLRGHDQYAYDGKDYIALNEDLRSWTAADTAAQITQRKW

EAAREAEQRRAYLEGECVEWLRRYLENGKDKLERADPPKTHVTHHPISD

HEATLRCWALGFYPAEITLTWQRDGEDQTQDTELVETRPAGDRTFQKWA

AVVVPSGEEQRYTCHVQHEGLPKPLTLRWE.

In certain embodiments of the compositions of the disclosure, the MHC is a class I MHC. The α-chain of the MHC may be encoded by sequence derived from an HLA-C gene, and specifically, HLA-C*07:02. The amino acid sequence of HLA-C*07:02 may comprise or consist of:

(SEQ ID NO: 3)
SHSMRYFDTAVSRPGRGEPRFISVGYVDDTQFVRFDSDAASPRGEPRAP

WVEQEGPEYWDRETQKYKRQAQADRVSLRNLRGYYNQSEDGSHTLQRMS

GCDLGPDGRLLRGYDQSAYDGKDYIALNEDLRSWTAADTAAQITQRKLE

AARAAEQLRAYLEGTCVEWLRRYLENGKETLQRAEPPKTHVTHHPLSDH

EATLRCWALGFYPAEITLTWQRDGEDQTQDTELVETRPAGDGTFQKWAA

VVVPSGQEQRYTCHMQHEGLQEPLTLSWE.

In certain embodiments of the compositions of the disclosure, HLA-A*11:01, HLA-B*07:02, and HLA-C*07:02 amino acid sequences from the UniProt database were truncated to remove the hinge, transmembrane and cytoplasmic regions at the C-terminal end and leader peptide sequence from N-terminal end.

In certain embodiments of the compositions of the disclosure, the MHC is a class II MHC.

In certain embodiments of the compositions of the disclosure, wherein the MHC is a class II MHC, the α-chain of the MHC may be truncated. For example, in certain embodiments, the α-chain of the MHC does not include a transmembrane region or a cytoplasmic region. In certain embodiments wherein the MHC is a class II MHC, the α-chain of the MHC comprises an $α_1$ domain and an $α_2$ domain. In certain embodiments wherein the MHC is a class II MHC, the α-chain of the MHC may be encoded by a sequence derived from a HLA gene selected from the group consisting of an HLA-DM gene, an HLA-DO gene, and HLA-DP gene, an HLA-DQ gene and an HLA-DR gene. In certain embodiments wherein the MHC is a class II MHC, the β-chain of the MHC is truncated. For example, in certain embodiments, the β-chain of the MHC does not include a transmembrane region or a cytoplasmic region. In certain embodiments wherein the MHC is a class II MHC, the β-chain of the MHC comprises a $β_1$ domain and a $β_2$ domain. In certain embodiments wherein the MHC is a class II MHC, the β-chain of the MHC may be encoded by a sequence derived from an HLA gene selected from the group consisting of an HLA-DM gene, an HLA-DO gene, and HLA-DP gene, an HLA-DQ gene and an HLA-DR gene.

In certain embodiments of the compositions of the disclosure, the MHC and/or the at least one assembly comprise(s) a carrier molecule. Carrier molecules of the disclosure facilitate integration of the MHC components with each peptide on the surface to form at least one peptide-MHC assembly. Although there are many mechanisms by which this facilitation may be accomplished, in certain embodiments, a carrier molecule of the disclosure may bind to one or more components of an MHC prior to the one or more components contacting the peptide on the surface. Carrier molecules that bind to one or more components of an MHC prior to the one or more components contacting the peptide on the surface do not bind those residues and/or binding sites of the one or more components that are essential for the peptide to bind to the one or more components of the MHC. Carrier molecules may remain bound to the fully-assembled MHC on the surface or they may dissociate once the components of the MHC assemble with the peptide on the surface. Carrier molecules of the disclosure do not alter the response of a T-cell to a peptide presented by the MHC on the surface.

In certain embodiments of the compositions of the disclosure, the carrier molecule may comprise, consist essentially of or consist of bovine serum albumin (BSA). In certain embodiments wherein the MHC is a class I MHC, the carrier molecule may comprise, consist essentially of or consist of bovine serum albumin (BSA).

In certain embodiments of the compositions of the disclosure, the linker comprises hexanoic acid. In certain embodiments, the linker may comprise between 1 and 5 monomer units. In certain embodiments, the linker may comprise between 3 and 5 monomer units. In certain embodiments, the linker may comprise at least one negatively-charged monomer unit. For example, the at least one negatively-charged monomer unit may comprise a negatively-charged amino acid. The negatively-charged amino acid may be Aspartate (D) or Glutamate (E). In certain embodiments, the linker may comprise hexanoic acid and at least one negatively-charged amino acid, having a length of 5 monomers. Exemplary linkers include, but are not limited to, (Surface)-5HEX, (Surface)-HEX-E-3HEX, (Surface)-HEX-D-3HEX, (Surface)-2HEX-E-HEX.

In certain embodiments of the compositions of the disclosure, the linker comprises polyethylene glycol (PEG). In certain embodiments, the linker may comprise between 1 and 5 monomer units. In certain embodiments, the linker may comprise between 3 and 5 monomer units. In certain embodiments, the linker may comprise at least one negatively-charged monomer unit. For example, the at least one negatively-charged monomer unit may comprise a negatively-charged amino acid. The negatively-charged amino acid may be Aspartate (D) or Glutamate (E).

In certain embodiments of the compositions of the disclosure, the linker comprises a mixture of Glycine (G) and Serine (S) amino acids. For example, the linker may comprise a mixture of Glycine (G):Serine (S) amino acids in a ratio of 3:1. In certain embodiments, the linker may comprise between 1 and 5 monomer units. In certain embodiments, the linker may comprise between 3 and 5 monomer units. In certain embodiments, the linker may comprise at least one negatively-charged monomer unit. For example, the at least one negatively-charged monomer unit may comprise a negatively-charged amino acid. The negatively-charged amino acid may be Aspartate (D) or Glutamate (E).

In certain embodiments of the compositions of the disclosure, the linker comprises at least one negatively-charged monomer unit and the assembly comprises an MHC encoded by an HLA2 gene. In certain embodiments, the linker comprises at least one negatively-charged monomer unit, the linker consists of between 3 and 5 monomers, and the assembly comprises an MHC encoded by an HLA2 gene. In certain embodiments, the linker comprises at least one negatively-charged monomer unit, the linker consists of 3 monomers, and the assembly comprises an MHC encoded by an HLA2 gene. In certain embodiments, the linker comprises at least one negatively-charged monomer unit, the linker consists of 5 monomers, and the assembly comprises an MHC encoded by an HLA2 gene.

In certain embodiments of the compositions of the disclosure, the each peptide of the at least one assembly or the plurality of assemblies may comprise, consist essentially of or consist of between 6 and 30 amino acids, inclusive of the endpoints. In certain embodiments of the compositions of the disclosure, each peptide of the at least one assembly or the plurality of assemblies may comprise, consist essentially of or consist of between 6 and 20 amino acids, inclusive of the endpoints. In certain embodiments of the compositions of the disclosure, each peptide of the at least one assembly or the plurality of assemblies may comprise, consist essentially of or consist of between 6 and 12 amino acids, inclusive of the endpoints. In certain embodiments of the compositions of the disclosure wherein the MHC is a class I MHC, each peptide of the at least one assembly or the plurality of assemblies may comprise, consist essentially of or consist of between 6 and 12 amino acids, inclusive of the endpoints. In certain embodiments of the compositions of the disclosure, each peptide of the at least one assembly or the plurality of assemblies may comprise, consist essentially of or consist of 9 amino acids. In certain embodiments of the compositions of the disclosure wherein the MHC is a class I MHC, each peptide of the at least one assembly or the plurality of assemblies may comprise, consist essentially of or consist of 9 amino acids. In certain embodiments of the compositions of the disclosure, each peptide of the at least one assembly or the plurality of assemblies may comprise, consist essentially of or consist of between 12 and 30 amino acids, inclusive of the endpoints. In certain embodiments of the compositions of the disclosure wherein the MHC is a class II MHC, each peptide of the at least one assembly or the plurality of assemblies may comprise, consist essentially of or consist of between 12 and 30 amino acids, inclusive of the endpoints.

In certain embodiments of the compositions of the disclosure, the peptide of the at least one assembly is synthesized in situ using a digital micromirror device (DMD). In certain embodiments of the compositions of the disclosure, the peptide of the plurality of assemblies is synthesized in situ using a digital micromirror device (DMD). In certain embodiments, the DMD comprises at least one micromirror. In certain embodiments, the DMD comprises a plurality of micromirrors. In certain embodiments, each micromirror corresponds to a microarea of the surface, wherein the micromirror corresponding to the microarea directs the synthesis of each peptide in the microarea. In certain embodiments, the surface comprises a plurality of microareas, wherein the number of micromirrors equals the number of microareas. As used herein, the term "microarea" is meant to describe a virtual boundary rather than a physical boundary existing on the surface itself. Although a micromirror may direct the synthesis of a peptide in any part of the surface, the microarea influenced by the micromirror is preferably positioned on the surface to vertically align with the micromirror. Thus the microarea influenced by a micromirror may lie directly beneath the micromirror or within a number of millimeters or centimeters from the vertical alignment of the edges of the micromirror.

In certain embodiments of the compositions of the disclosure, and particularly, those in which the peptide is synthesized in situ using a digital micromirror device (DMD), each microarea may comprise between $10^3$ and $10^8$ peptides. In certain embodiments, the surface may have a density of $1.24 \times 10^{13}$ amines per $cm^2$, wherein the amine is the first functional group attached to the surface, to which the linker and peptide will subsequently couple during in situ synthesis. When the surface has a density of $1.24 \times 10^{13}$ amines per $cm^2$, the surface may comprise at least $10^6$ peptides, corresponding to at least $10^6$ peptide-MHC assemblies. When the surface has a density of $1.24 \times 10^{13}$ amines per $cm^2$, the surface may comprise between $10^3$ and $10^8$ "unique" peptides per micromirror. When the surface has a density of $1.24 \times 10^{13}$ amines per $cm^2$, the surface may comprise between $10^3$ and $10^8$ "unique" peptides per microarea when each microarea corresponds to a single micromirror. The term "unique peptide" is meant to describe a unique peptide sequence. In addition to unique peptides, each micromirror may produce replicate peptides, or, in other words, a plurality of peptides having the same sequence, but produced by a unique program or feature (a set of instructions) directing the micromirror to synthesize a peptide having a unique sequence among the peptides of the same surface or section of the same surface.

In certain embodiments of the compositions of the disclosure, and particularly, those in which the peptide is synthesized in situ using a digital micromirror device (DMD), a first microarea comprises at least a first peptide having a unique amino acid sequence when compared to the amino acid sequence of at least a second or subsequent peptide within each second or subsequent microarea. In certain embodiments, the first microarea comprising at least one peptide having a unique amino acid sequence further comprises at least one replicate of the peptide having a unique amino acid sequence. For example, the second or subsequent microarea may be juxtaposed to the first microarea. By juxtaposed, it is meant that the virtual boundaries of the first and the second microareas are physically juxtaposed (e.g. neighboring microareas). In certain embodiments, the first microarea comprises at least a first peptide having a unique amino acid sequence when compared to the amino acid sequence of at least a second or subsequent peptide within each second or subsequent microarea juxtaposed to the first microarea. In certain embodiments, the first microarea comprises at least a first peptide having a unique amino acid sequence when compared to the amino acid sequence of at least a second or subsequent peptide within each second or subsequent microarea on the surface.

In certain embodiments of the compositions of the disclosure, and particularly, those in which the peptide is synthesized in situ using a digital micromirror device (DMD), the surface may comprise up to $1.24 \times 10^{13}$ peptides per square centimeter.

In certain embodiments of the compositions of the disclosure, the surface comprises two or more sections. In certain embodiments of the compositions of the disclosure, the surface comprises between 2 and 48 sections, inclusive of the endpoints.

In certain embodiments of the compositions of the disclosure, the composition further comprises at least one T-cell. In certain embodiments of the compositions of the disclosure, the composition further comprises at least one T-cell per section. Optionally, the at least one T-cell may be bound to the surface.

In certain embodiments, compositions of the disclosure may further comprise a detectable agent that recognizes a molecule released from the at least one T-cell upon activation of the at least one T-cell by at least one peptide on the surface. The detectable agent may be any organic or inorganic molecule with a detectable label capable of specifically binding to at least one molecule released from the at least one T-cell upon activation. In certain embodiments, the detectable agent is an antibody. While the molecule released from the at least one T-cell may be any molecule of the cell's secretome, in certain embodiments, the molecule released from the at least one T-cell is a cytokine. Examples of cytokines include, but are not limited to, interleukin 2 (IL-2), interleukin 3 (IL-3), interleukin 4 (IL-4), interleukin 5 (IL-5), interleukin 6 (IL-6), granulocyte-macrophage colony-stimulating factor (GM-CSF), and interferon-gamma (INFγ).

In certain embodiments, compositions of the disclosure may comprise at least 2 surfaces. Surfaces of the compositions of the disclosure may be flat. For example, the surface of a composition of the disclosure may be a chip, plate or slide.

In certain embodiments, compositions of the disclosure may comprise at least 2 surfaces. Surfaces of the compositions of the disclosure may be curved, convex, or concave. In certain embodiments, the surface is a bead.

In certain embodiments of the compositions of the disclosure, each peptide of the plurality of assemblies is synthesized on the surface to generate a spatially-ordered array. In the context of synthesis using DMD technology, each micromirror has a unique program for reflecting light on the surface or for deflecting light away from the surface. Peptides on the surfaces of the disclosure may be synthesized using photoprotected amino acids. When a micromirror directs light at the surface, the last amino acid added to the growing peptide is deprotected and become available to bind to another amino acid. By providing a unique sequence of movements to each micromirror (also referred to as a "job"), the DMD can synthesize at least one unique peptide sequence corresponding to each micromirror. By preprogramming the mirrors in a predetermined pattern, the sequence of each peptide synthesized on the surface is known by its relative position to the micromirror used to synthesize it.

In certain embodiments, the surface is a chip and three chips are placed on a slide for simultaneous manufacture and use. In certain embodiments the spatial arrangement of the plurality of peptides on each of these three chips may be identical to provide experimental replicates. In certain embodiments the spatial arrangement of the plurality of peptides on each of these three chips may be distinct to provide a higher throughput assay.

The disclosure provides a method of making a composition of the disclosure, comprising contacting a surface comprising at least one peptide and an MHC composition under conditions suitable for generating at least one peptide-MHC assembly, wherein the peptide in an integral component of the assembly, wherein the at least one peptide is attached to the surface at its C-terminus through a linker and wherein the at least one peptide is synthesized on the surface. In certain embodiments, the at least one assembly is a plurality of assemblies.

In certain embodiments of the methods of making a composition of the disclosure, prior to the contacting step, the surface may be treated with a binding buffer. In certain embodiments, the binding buffer comprises 1% casein, 10 mM Tris pH 7.4, and 0.25% Tween. Optionally, the binding buffer may further comprise a blocking agent.

In certain embodiments of the methods of making a composition of the disclosure, the surface and the MHC composition remain in contact for a period of between 8 and 24 hours, inclusive of the endpoints. In certain embodiments of the methods of making a composition of the disclosure, the surface and the MHC composition remain in contact for a period of about 12 hours. The contacting step may occur at room temperature. Alternatively, the contacting step may occur at 4° C.

In certain embodiments of the methods of making a composition of the disclosure, the MHC composition comprises BSA, a solubilized β2-microglobulin (β2m) and a solubilized α-chain. In certain embodiments, the MHC composition comprises a solubilized α-chain:solubilized β2m mole:mole ratio of between 1:1 and 1:2, inclusive of the endpoints. The solubilized α-chain may be encoded by an HLA-A gene, an HLA-B gene or an HLA-C gene. In certain embodiments, the solubilized α-chain is produced by a method comprising the steps of: (a) reverse translating an amino acid sequence encoding the solubilized α-chain into a codon-optimized deoxyribonucleic acid (DNA) sequence, (b) synthesizing the codon-optimized deoxyribonucleic acid (DNA) sequence as a double stranded DNA molecule, (c) expressing the double stranded DNA molecule in the form of an inclusion body to produce an α-chain, and (d) solubilizing the α-chain. In certain embodiments of the method of producing the solubilized α-chain, the codon-optimized deoxyribonucleic acid (DNA) sequence is optimized for expression in *E. coli*. In certain embodiments of the method of producing the solubilized α-chain, the expressing step comprises cloning the double stranded DNA molecule into an expression vector, wherein, optionally, the expression vector is a plasmid.

In certain embodiments of the methods of making a composition of the disclosure, the MHC composition comprises a carrier molecule, a solubilized β-chain and a solubilized α-chain. In certain embodiments wherein the MHC is a class II MHC, the carrier molecule may be an invariant chain, a CLIP, a CD74 peptide or a functional fragment thereof. In certain embodiments wherein the MHC is a class II MHC, the carrier molecule may be BSA.

In certain embodiments of the methods of making a composition of the disclosure, the MHC composition comprises between 0.1% and 10% BSA, inclusive of the endpoints. The MHC composition may comprise between 1% and 5% BSA, inclusive of the endpoints. The MHC composition may comprise between 2% and 3% BSA, inclusive of the endpoints. Optionally, the BSA is formulated in a BSA buffer. In certain embodiments, the BSA buffer comprises 20 mM Tris-HCl at pH 7.8.

In certain embodiments of the methods of making a composition of the disclosure, the MHC composition may further comprise a buffer. The MHC buffer may comprise 10 mM Tris-HCl at pH 8.5.

In certain embodiments of the methods of making a composition of the disclosure, prior to contacting the surface, the MHC composition is produced by a method comprising the steps of: (a) incubating the MHC composition at 4° C. overnight, (b) separating a precipitate from the MHC composition, and (c) collecting the precipitate-free MHC composition for contacting the surface. In certain embodiments, the separating step may comprise a centrifugation step wherein the precipitate-free MHC composition is a supernatant produced from the centrifugation. In certain embodiments of the separating step, the collecting step further comprises concentrating the precipitate-free MHC composition. In certain embodiments, the collecting step further comprises filtering the precipitate-free MHC composition.

The disclosure provides a use of a composition of the disclosure for the identification of one or more peptide antigens that are immunodominant when presented by an MHC in vivo. For example, the disclosure provides a use of a composition of the disclosure for the identification of one or more peptide antigens that are immunodominant when presented by an MHC in vivo comprising (a) contacting at least one T-cell and the composition and (b) detecting at least one molecule secreted from the at least one T-cell upon activation of the T-cell, thereby identifying one or more peptide antigens that are immunodominant when presented by an MHC in vivo. In certain embodiments of this use, the immunodominant peptide antigens are immunogenic.

In certain embodiments of the use of a composition of the disclosure for the identification of one or more peptide antigens that are immunodominant when presented by an MHC in vivo the MHC is a class I MHC.

In certain embodiments of the use of a composition of the disclosure for the identification of one or more peptide antigens that are immunodominant when presented by an MHC in vivo the MHC is a class II MHC.

In certain embodiments of the use of a composition of the disclosure for the identification of one or more peptide antigens that are immunodominant when presented by an MHC in vivo the peptide antigen is a neoantigen. In certain embodiments, the neoantigen may comprise one or more amino acid(s) essential for binding the MHC. In certain embodiments, one or more amino acid(s) of the neoantigen that are not essential for binding the MHC ("non-essential" amino acids) may comprise(s) one or more substitution(s) of the amino acid sequence compared to a wild type sequence of the peptide.

In certain embodiments of the use of a composition of the disclosure for the identification of one or more peptide antigens that are immunodominant when presented by an MHC in vivo the peptide antigen is a self-antigen. In certain embodiments, the self-antigen stimulates a T-cell and induces an autoimmune response.

The disclosure provides a use of a self-antigen of the disclosure identified as immunodominant when presented by an MHC in vivo, a sequence complementary to the self-antigen, an antibody that specifically binds the self-antigen, or a chimeric antigen receptor that specifically binds the self-antigen for the manufacture of a medicament to reduce or prevent an autoimmune response.

In certain embodiments of the use of a composition of the disclosure for the identification of one or more peptide antigens that are immunodominant when presented by an MHC in vivo the peptide antigen is a cancer antigen. In certain embodiments, the cancer antigen stimulates a T-cell and induces an immune response. The T-cell may be genetically-modified. For example, the T-cell may comprise a genetically-modified T-cell receptor that specifically binds the cancer antigen. In certain embodiments, the T-cell may comprise a chimeric antigen receptor that specifically binds the cancer antigen.

The disclosure provides a vaccine comprising a cancer antigen of the disclosure identified as immunodominant when presented by an MHC in vivo.

The disclosure provides a use of a cancer antigen of the disclosure identified as immunodominant when presented by an MHC in vivo, a sequence complementary to the cancer antigen, an antibody that specifically binds the cancer antigen, or a chimeric antigen receptor that specifically binds the cancer antigen for the manufacture of a medicament to enhance or induce an immune response.

In certain embodiments of the use of a composition of the disclosure for the identification of one or more peptide antigens that are immunodominant when presented by an MHC in vivo the peptide antigen is a bacterial, a viral, or a microbial antigen.

In certain embodiments of the use of a composition of the disclosure for the identification of one or more peptide antigens that are immunodominant when presented by an MHC in vivo the peptide antigen is a viral antigen, wherein the viral antigen stimulates a T-cell and induces an immune response. In certain embodiments, the viral antigen is derived from a cytomegalovirus (CMV). The T-cell may be genetically-modified. For example, the T-cell may comprise a genetically-modified T-cell receptor that specifically binds the viral antigen. In certain embodiments, the T-cell may comprise a chimeric antigen receptor that specifically binds the viral antigen.

The disclosure provides a vaccine comprising a viral antigen of the disclosure identified as immunodominant when presented by an MHC in vivo. In certain embodiments, the viral antigen is derived from a cytomegalovirus (CMV).

The disclosure provides a use of a viral antigen of the disclosure identified as immunodominant when presented by an MHC in vivo, a sequence complementary to the viral antigen, an antibody that specifically binds the viral antigen, or a chimeric antigen receptor that specifically binds the viral antigen for the manufacture of a medicament to enhance or induce an immune response. In certain embodiments, the viral antigen is derived from a cytomegalovirus (CMV).

In certain embodiments of the use of a composition of the disclosure for the identification of one or more peptide antigens that are immunodominant when presented by an MHC in vivo the peptide antigen is a bacterial antigen, wherein the bacterial antigen stimulates a T-cell and induces an immune response. The T-cell may be genetically-modified. For example, the T-cell may comprise a genetically-modified T-cell receptor that specifically binds the bacterial antigen. In certain embodiments, the T-cell may comprise a chimeric antigen receptor that specifically binds the bacterial antigen.

The disclosure provides a vaccine comprising a bacterial antigen of the disclosure identified as immunodominant when presented by an MHC in vivo.

The disclosure provides a use of a bacterial antigen of the disclosure identified as immunodominant when presented by an MHC in vivo, a sequence complementary to the bacterial antigen, an antibody that specifically binds the bacterial antigen, or a chimeric antigen receptor that specifically binds the bacterial antigen for the manufacture of a medicament to enhance or induce an immune response.

In certain embodiments of the use of a composition of the disclosure for the identification of one or more peptide antigens that are immunodominant when presented by an MHC in vivo the peptide antigen is a microbial antigen, wherein the microbial antigen stimulates a T-cell and induces an immune response. The T-cell may be genetically-modified. For example, the T-cell may comprise a genetically-modified T-cell receptor that specifically binds the microbial antigen. In certain embodiments, the T-cell may comprise a chimeric antigen receptor that specifically binds the microbial antigen.

The disclosure provides a vaccine comprising a microbial antigen of the disclosure identified as immunodominant when presented by an MHC in vivo.

The disclosure provides a use of a microbial antigen of the disclosure identified as immunodominant when presented by an MHC in vivo, a sequence complementary to the microbial antigen, an antibody that specifically binds the microbial antigen, or a chimeric antigen receptor that specifically binds the microbial antigen for the manufacture of a medicament to enhance or induce an immune response.

The disclosure provides a use of a composition of the disclosure for the identification of at least one T-cell stimulated by at least one peptide comprising (a) contacting the least one T-cell and the composition, (b) detecting at least one molecule secreted from the at least one T-cell upon activation, and (c) imaging the at least one T-cell.

In certain embodiments of the of a composition of the disclosure for the identification of at least one T-cell stimulated by at least one peptide, the at least one T-cell is not genetically-modified.

In certain embodiments of the of a composition of the disclosure for the identification of at least one T-cell stimulated by at least one peptide, the at least one T-cell is genetically-modified. For example, in certain embodiments, the at least one T-cell may comprise a modified T-cell receptor that specifically binds the at least one peptide. In certain embodiments, the at least one T-cell comprises a chimeric antigen receptor (CAR) that specifically binds the at least one peptide.

In certain embodiments of the of a composition of the disclosure for the identification of at least one T-cell stimulated by at least one peptide, the imaging step comprises contacting the at least one T-cell with one or more detectable agents that recognize one or more cell-surface markers. The detectable agent may be any organic or inorganic molecule with a detectable label capable of specifically binding to at least one molecule released from the at least one T-cell upon activation. In certain embodiments, the detectable agent is an antibody. Examples of cell-surface markers include, but are not limited to, CD34, CD45, CD15, CD14, CD3, CD19, CD61, CD4, CD8 and CD25. For example a stem cell may be identified by expression of CD34. A granulocyte may be identified by expression of CD45 and CD15. A monocyte may be identified by expression of CD45 and CD14. A T-cell (also referred to as a T-lymphocyte) may be identified by expression of CD45 and CD3. A B-cell (also referred to as a B-lymphocyte) may be identified by expression of CD45 and CD19. A thrombocyte may be identified by expression of CD45 and CD61. Among T-cells, a helper T-cell may be identified by expression of CD45, CD3 and CD4. Among T-cells, a cytotoxic T-cell may be identified by expression of CD45, CD3 and CD8. Among T-cells, an activated T-cell may be identified by expression of CD45, CD3 and CD25.

In certain embodiments of the compositions and methods of the disclosure for the identification of at least one T-cell stimulated by at least one peptide, the at least one T-cell may be comprised in a cell population. The cell population may be isolated from any biological fluid, including, but not limited to, whole blood, blood serum, blood plasma, peripheral blood, umbilical cord blood, lymph fluid, cerebral spinal fluid (CSF), and amniotic fluid. The cell population may be isolated from any biological tissue, including, but not limited to, lymph tissue, bone marrow, tumor tissue, and biopsy tissue. The cell population may be homogeneous or heterogeneous. The cell population may comprise, consist essentially of or consist of immune cells or T-cells. The cell population may comprise, consist essentially of or consist of a mixture of helper and cytotoxic T-cells prior to contacting a composition of the disclosure. In certain embodiments, the cell population does not comprise any activated T-cells prior to contacting a composition of the disclosure. Thus, the invention provides a composition comprising at least one assembly or a plurality of assemblies comprising a peptide and a major histocompatibility complex (MHC), wherein the peptide is an integral component of the MHC, wherein the peptide is attached to a surface at its C-terminus through a linker and wherein the peptide is synthesized on the surface.

The MHC may be a class I or class II MHC. It may comprise a carrier molecule, which may be bovine serum albumin (BSA). The linker may comprise hexanoic acid, polyethylene glycol (PEG) or a mixture of Glycine (G) and Serine (S) amino acids, which may have a ratio of 3:1. The linker may comprise between 1 and 5 monomer units, preferably between 3 and 5 monomer units. The linker may also comprise at least one negatively-charged monomer unit, which may be a negatively-charged amino acid such as Aspartate (D) or Glutamate (E). In one embodiment, the linker comprises hexanoic acid and at least one of Aspartate (D) or Glutamate (E), preferably within 5 monomer units.

The MHC may be encoded by a human leukocyte antigen 2 (HLA2) gene, by another a human leukocyte antigen (HLA) gene, by a mammalian leukocyte antigen gene, by a primate leukocyte antigen gene, by a mouse leukocyte antigen (MLA) gene, or by a human leukocyte antigen (HLA) gene and wherein an α-chain of the MHC is truncated. In the latter case, the α-chain does not include a transmembrane region or a cytoplasmic region. The α-chain may not include a hinge region. The α-chain may comprise an α1 domain, an α2 domain and an α3 domain. The α-chain may be encoded by a sequence derived from an HLA gene selected from the group consisting of an HLA-A gene, an HLA-B gene, an HLA-C gene, an HLA-E gene, an HLA-F gene, an HLA-G gene, an HLA-K pseudogene and an HLA-L pseudogene. The α-chain may also be encoded by a sequence derived from an HLA gene selected from the group consisting of an HLA-A gene, an HLA-B gene and an HLA-C gene. An α-chain may also comprise an α1 domain and an α2 domain. In one embodiment, the α-chain may be encoded by a sequence derived from an HLA gene selected from the group consisting of an HLA-DM gene, an HLA-DO gene, and HLA-DP gene, an HLA-DQ gene and an HLA-DR gene.

A β-chain of the MHC may also be truncated, for example it may not include a transmembrane region or a cytoplasmic region. The β-chain may comprise a β1 domain and a β2 domain. The β-chain may be encoded by a sequence derived from an HLA gene selected from the group consisting of an HLA-DM gene, an HLA-DO gene, and HLA-DP gene, an HLA-DQ gene and an HLA-DR gene.

Each peptide of the plurality of assemblies may consist between 6 and 30, preferably between 6 and 20, more preferably between 6 and 12 and most preferably 9 amino acids, inclusive of the endpoints. The peptide of the at least one assembly may be synthesized in situ using a digital micromirror device (DMD), wherein each micromirror corresponds to a microarea of the surface and wherein the micromirror corresponding to the microarea directs the synthesis of each peptide in the microarea.

In this context, the present invention also provides method of making accomposition disclosed above the method comprising contacting a surface comprising at least one peptide and an MHC composition under conditions suitable for generating at least one peptide-MHC assembly, wherein the peptide is an integral component of the MHC, wherein the peptide is attached to the surface at its C-terminus through a linker and wherein the peptide is synthesized on the surface. Prior to the contacting step, the surface may be treated with a binding buffer, for example a buffer comprising 1% casein, 10 mM Tris pH 7.4, and 0.25% Tween 20 and optionally a blocking reagent. The surface and the MHC composition may remain in contact for a period of between 8 and 24 hours, inclusive of the endpoints, for example for about 12 hours, for example at room temperature or 4° C. The MHC composition may comprise BSA, a solubilized β2-microglobulin (β2m) and a solubilized α-chain. Said composition may also comprise a carrier molecule, a solubilized β-chain and a solubilized α-chain. The carrier molecule may be an invariant chain, a CLIP, a CD74 peptide or a functional fragment thereof, or bovine serum albumin (BSA) preferably between 0.1% and 10% BSA, more preferably between 1% and 5% BSA and most preferably between 2% and 3% BSA, inclusive of the endpoints. The BSA may be formulated in a BSA buffer, which for example comprises 20 mM Tris-HCl at pH 7.8. Also, the MHC composition further comprises a buffer, for example 10 mM Tris-HCl at pH 8.5.

Prior to contacting the surface, the MHC composition is produced by a method comprising the steps of: (a) incubating the MHC composition at 4° C. overnight, (b) separating a precipitate from the MHC composition, and (c) collecting the precipitate-free MHC composition for contacting the surface.

The separating step may further comprise a centrifugation step wherein the precipitate-free MHC composition is a supernatant produced from the centrifugation.

The collecting step may further comprise concentrating the precipitate-free MHC composition. The collecting step may further comprise filtering the precipitate-free MHC composition. The MHC composition may comprises a solubilized α-chain:solubilized β2m mole:mole ratio of between 1:1 and 1:2, inclusive of the endpoints. The solubilized α-chain may be encoded by an HLA-A gene, an HLA-B gene or an HLA-C gene. Said solubilized α-chain is produced by a method comprising the steps of: (a) reverse translating an amino acid sequence encoding the solubilized α-chain into a codon-optimized deoxyribonucleic acid (DNA) sequence, (b) synthesizing the codon-optimized deoxyribonucleic acid (DNA) sequence as a double stranded DNA molecule, (c) expressing the double stranded DNA molecule in the form of an inclusion body to produce an α-chain, and (d) solubilizing the α-chain.

Optionally, the codon-optimized deoxyribonucleic acid (DNA) sequence is optimized for expression in *E. coli*.

A composition as disclosed above may be used for the identification of one or more peptide antigens that are immunodominant when presented by an MHC in vivo, and, optionall, immunogenic. The MHC may be a class I or II MHC, the peptide antigen may be a neoantige, which may comprise one or more amino acid(s) essential for binding the MHC. One or more amino acid(s) of the neoantigen that are not essential for binding the MHC may comprise one or more substitution of the amino acid sequence compared to a wild type sequence of the peptide. The peptide antigen may also be a self-antigen, which may stimulate a T-cell and induces an autoimmune response.

The self-antigen, a sequence complementary to the self-antigen, an antibody that specifically binds the self-antigen, or a chimeric antigen receptor that specifically binds the self-antigen may be used for the manufacture of a medicament to reduce or prevent an autoimmune response.

The peptide antigen may be a cancer antigen, which may stimulate a T-cell and induces an immune response and may be included into a vaccine. The cancer antigen a sequence complementary to the cancer antigen, an antibody that specifically binds the cancer antigen, or a chimeric antigen receptor that specifically binds the cancer antigen may also be used for the manufacture of a medicament to enhance or induce an immune response. The T-cell may be genetically-modified and may comprise a genetically-modified T-cell receptor that specifically binds the cancer antigen The T-cell may also comprise a chimeric antigen receptor that specifically binds the cancer antigen.

The peptide antigen may also be a bacterial, a viral, or a microbial antigen. A viral antigen may stimulate a T-cell and induce an immune response. The viral antigen may be derived from a cytomegalovirus (CMV) and/or may serve as a vaccine or part of a vaccine. The viral antigen, a sequence complementary to the viral antigen, an antibody that specifically binds the viral antigen, or a chimeric antigen receptor that specifically binds the viral antigen may be used for the manufacture of a medicament to enhance or induce an immune response. The T-cell may be genetically-modified and may comprise a genetically-modified T-cell receptor that specifically binds the viral antigen. The T-cell may comprise a chimeric antigen receptor that specifically binds the viral antigen.

Also, a bacterial antigen and wherein the bacterial antigen stimulate a T-cell and induce an immune response so that it may serve as vaccine or part of a vaccine. A sequence complementary to the bacterial antigen, an antibody that specifically binds the bacterial antigen, or a chimeric antigen receptor that specifically binds the bacterial antigen may be used for the manufacture of a medicament to enhance or induce an immune response. The T-cell may be genetically-modified and may comprise a genetically-modified T-cell receptor that specifically binds the bacterial antigen. It may also comprise a chimeric antigen receptor that specifically binds the bacterial antigen.

A composition as disclosed above may also be used for the identification of at least one T-cell stimulated by at least one peptide of the composition comprising (a) contacting the least one T-cell and the composition, (b) detecting at least one molecule secreted from the at least one T-cell upon activation, and (c) imaging the at least one T-cell.

At least one T-cell may be genetically-modified and the at least one T-cell may comprise a modified T-cell receptor that specifically binds the at least one peptide of the composition. It may also comprise achimeric antigen receptor (CAR) that specifically binds the at least one peptide of the composition. The imaging step may comprise contacting the at least one T-cell with one or more detectable agents that recognize one or more cell-surface markers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 is a plot depicting the HLA-A2 loading specificity for a well-studied Vaccinia Virus Peptide LMYDIINSV (SEQ ID NO: 8) assembled with HLA-A2. The specificity of interaction of key residues can be seen on the substitution plot. Each amino acid of the 9 amino acid peptide was substituted for each of the 20 possible amino acids to identify those positions within this peptide that are essential for forming a proper peptide-MHCI complex. The figure shows all 20 amino acids in a line by their single amino acid letter codes, grouped by characteristics: AFILMVWPGSYCQTNRKHDE. The amino acids A, F, I, L, M, V, W and P are nonpolar amino acids. The amino acids G, S, Y, C, Q, T, N are polar amino acids. The amino acids R, K and H are basic amino acids. The amino acids D and E are acidic amino acids.

FIG. 10A is a plot depicting the HLA-A2/RLYDYFTRV peptide-MHC assembly formation ("RLYDYFTRV" is disclosed as SEQ ID NO: 10) using a standard 5HEX linker. Binding was performed at pH 6.5 at 4° C. overnight.

FIG. 10B is a plot depicting the HLA-A2/RLYDYFTRV peptide-MHC assembly formation ("RLYDYFTRV" is disclosed as SEQ ID NO: 10) using a negatively charged HEX-asp-3HEX linker. Binding was performed at pH 6.5 at 4° C. overnight. Dashed lines show an increase in the peptide-MHC assembly signal for the original peptide sequence when a negatively charged linker is used as opposed to the standard 5HEX linker.

DETAILED DESCRIPTION

Figure 1A:
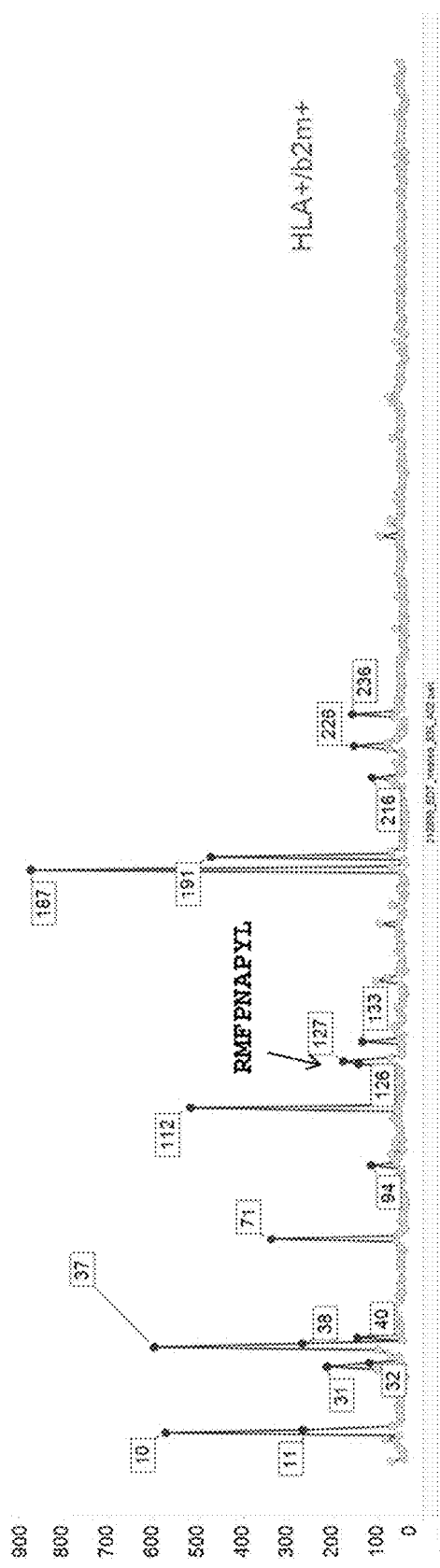
FIG. 1A-B is a pair of plots depicting fluorescence intensity as a function of position for pCy5-antibody (W6/32) labeled 9 mer peptide (SEQ ID NO: 7)-MHCI assembly, either with the b2m subunit (A)(top plot) or without the b2m subunit (B)(bottom plot, negative control). Example 1, SET 1, provides the experimental set-up for the composition from which this data is derived. For more information regarding the antibody, see Dao et al. (Science Translational Medicine 13 Mar. 2013: Vol. 5, Issue 176, pp. 176ra33).

T-cells (also known as Thymocytes cells or T lymphocytes) are a type of lymphocyte (a type of white blood cell) that play a central role in cell-mediated immunity, which involves the activation of phagocytes, antigen-specific cytotoxic T-lymphocytes, and the release of various cytokines in response to an antigen. Unlike antigen recognition by B cells, T-cell recognition of antigen does not involve direct binding to an offending antigen, but rather an interaction of T-cell receptors with the composite surface of a pathogen derived peptide epitope and the major histocompatibility complex (MHC) molecule that carries the epitope to the cell surface. It is estimated that the human immune system hosts around 25 million T-cell clones with distinct specificities, which defines an evolving, extensive repository of cellular immune responses against self- and foreign antigens. Therefore, it is of fundamental and therapeutic importance to detect and survey these T-cell populations. Unfortunately, the broad recognition potential of the human T-cell repertoire is poorly matched by the currently established methods for immune monitoring and T-cell epitope discovery.

The methods that are frequently used to analyze antigen specific T-cell responses include intracellular cytokine staining, CD107 cytotoxicity assay, ELISpot, killing assays, etc. These assays are all quite useful in terms of addressing certain T-cell functions, yet they are often labor intensive, require large quantities of clinical peripheral blood mononuclear cell (PBMC) specimens, and have poor spatial resolution and/or low sensitivity for secreted responses. Recently the staining of antigen-specific T-cells with fluorescently labeled multimeric peptide-MHC complexes (p/MHC) become extensively used for the analysis of T-cell responses against a small set of antigens. However, the synthesis of pMHC tetramers is time consuming and not easily scalable. As a result, only a limited number of pMHC complexes can be surveyed and therefore it is hard to track multiple T-cell specificities for different functional events.

To overcome the aforementioned limitations, the disclosure provides an array-based approach for the capture and characterization of TCRs, TCR-like antibodies and antigen-specific T-cells based on their adherence to p/MHC complexes.

Scalable peptide microarrays are a paradigm-shifting advancement in protein science. By using, for example, a digital micromirror device (DMD) to synthesize up to 2.9 million unique and spatially-ordered peptides on a single surface, it is possible to test thousands of targets simultaneously. In addition, the compositions and methods of the disclosure can incorporate peptides with modifications such as phosphorylation, non-natural amino acids such as citrulline, as well as constrained peptides (e.g. cyclic peptides).

Another unique feature of the compositions of the disclosure is the direct on-surface formation of p/MHC complex. Traditionally, when p/MHC complexes are studied in high-throughput format, each individual p/MHC complex is constructed first. As empty MHC molecules (without the presence of a proper peptide) are unstable, both the peptide and the MHC component need to be present in the folding reaction. The multimers are then formed and spotted onto treated and/or derivatized surfaces. This manufacturing process can become a really daunting task when multiple p/MHCs need to be studied. Moreover, by spotting p/MHCs onto treated and/or derivatized surfaces, existing technologies suffer from surface induced effects, including protein denaturation and protein adsorption in inactive orientations.

The methods of making the compositions of the disclosure overcome the technical hurdles of existing technologies by introducing a carrier molecule into the preparation process of the MHC α and β subunit mixture, which effectively rescues the proteins from denaturation even in the absence of proper MHC-binding peptides. The mixtures are then directly applied to array surfaces, where the existence of the bound peptides will result in MHC refolding. In this way, thousands and thousands of pMHCs are assembled simultaneously. T-cells, T-cell receptors (TCRs) (e.g. native and/or chimeric antigen receptors) or TCR-like antibodies may be applied the surface. Following an incubation, peptide target specific T-cells, for example, adhere to the corresponding p/MHC molecules, resulting in spatial separation of different antigen-specific T-cell/TCR populations. Because the readout of the assay is dependent on location rather than overall fluorescent signals, the compositions and methods of the disclosure are uniquely capable of performing highly multiplexed reactions.

Synthesis of Peptides In Situ

The synthesis of peptides or a plurality of peptides of the disclosure on the surface, in situ, carried out rapidly and efficiently using patterning processes. The process may be automated and computer controlled to allow the fabrication of a one or two-dimensional array of peptides. No lithographic masks are required, thus eliminating the significant costs and time delays associated with the production of lithographic masks and avoiding time-consuming manipulation and alignment of multiple masks during the fabrication process of peptide arrays.

Figure 9:
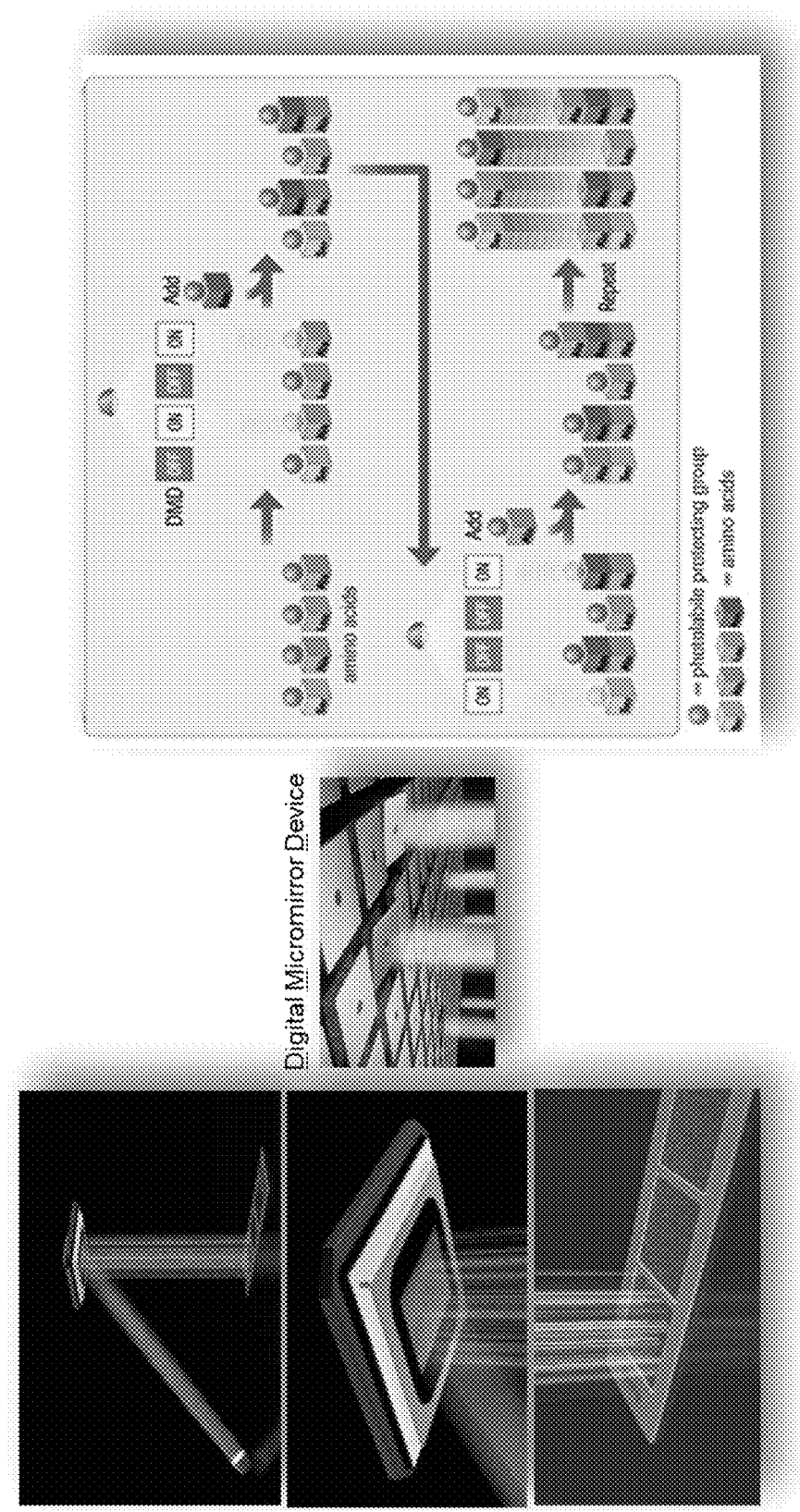
FIG. 9 is a series of schematic diagrams demonstrating how a Digital Micromirror Device (DMD) may be used to manufacture compositions of the disclosure by synthesizing each peptide on the surface in situ. The left panel depicts an exemplary DMD comprising a plurality of micromirrors positioned directly above one surface of a series of three surfaces that are contained on a glass slide. As light is shown onto the plurality of micromirrors, each micromirror of the plurality is independently programmed to tilt, either reflecting the light towards an area of the surface beneath the micromirror or to deflecting the light away from the area of the surface beneath the micromirror. The tilting of the individual micromirrors is depicted in the center panel. The right hand panel demonstrates how pulses of light regulated by the tilting of each micromirror build a peptide on the surface in situ. Peptides of the compositions of the disclosure are bound to the surface by a linker at their C-terminal end. Each amino acid added to the peptide comprises a photolabile protecting group that, in the absence of light, prevents the addition of another amino acid to the peptide. However, when light contacts the protecting group, the amino acid becomes deprotected and an amino acid may be added. As amino acids are flowed across the surface, each micromirror reflects light at a preprogrammed time to deprotect amino acids when the intended next amino acid in the peptide sequence is flowing across the surface. The area of the surface controlled by any given micromirror is referred to herein as a "microarea". A microarea of the disclosure has a virtual boundary rather than a physical one. As shown in the right-hand panel of this figure, in preferred embodiments of the surfaces of the disclosure, there are no physical boundaries to obstruct the flow of amino acids across the surface during peptide synthesis.

An active surface to which peptide synthesis linkers have been applied may be used to support the peptides that are to be fabricated. To initiate the active surface to provide a first level of amino acids, a high precision two-dimensional light image is projected onto the surface, illuminating those microareas (also referred to as pixels or tiles, in, for example, U.S. Pat. Nos. 6,375,903 and 8,030,477, the contents of which are each incorporated herein by reference) in the array on the active surface which are to be activated to couple to a first amino acid. The light incident on the microareas in the array to which light is applied de-protects bound the amino acid and makes them available for coupling to additional amino acids. After this development step, a fluid containing the appropriate amino acid is provided to the active surface and the selected amino acid couples to the exposed sites. The process is then repeated to couple to another amino acid to a different set of microarea locations, until all of the elements of the two-dimensional array on the surface have an appropriate amino acid coupled thereto (see, for example, FIG. 9). The amino acids bound on the substrate are protected, either with a chemical capable of binding to the amino acids or with a layer(s) of photoresist covering all of the bound amino acids, and a new array pattern is then projected and imaged onto the surface to activate the protecting material in those microareas to which the first new amino acid is to be added. These microareas are then exposed and a solution containing the selected amino acid is applied to the array so that the amino acid couples to the exposed microarea locations. This process is then repeated for all of the other microarea locations in the second level of amino acids. The process as described may then be repeated for each desired level of amino acids until the entire selected two-dimensional array of peptide sequences has been completed.

The image is projected onto the surface utilizing an image former having an appropriate light source that provides light to a micromirror device comprising a two-dimensional array of electronically addressable micromirrors, each of which can be selectively tilted between one of at least two separate positions. In one of the positions of each micromirror, the light from the source incident on the micromirror is deflected off an optical axis and away from the surface, and in a second of the at least two positions of each micromirror, the light is reflected along the optical axis and toward the surface. Projection optics receive the light reflected from the micromirrors and precisely image the micromirrors onto the active surface. Collimating optics may be used to collimate the light from the source into a beam provided directly to the micromirror array or to a beam splitter, wherein the beam splitter reflects a portion of the beam to the micromirror array and transmits reflected light from the micromirror array through the beam splitter. The light directly reflected from the micromirrors or transmitted through the beam splitter is directed to projection optics lenses which image the micromirror array onto the active surface. Because the selectively addressable micromirrors in the micromirror array may either fully reflect or fully deflect the light provided to them, the image of the micromirror array exhibits a very high contrast between the "on" and "off" microareas. The micromirrors may also be capable of being indexed to more than two positions, in which case additional optics may be provided to allow exposure of more than one surface using a single micromirror array device. In addition, the micromirrors are capable of reflecting light at any wavelength without damage to them, allowing short wavelength light, including light in the range of ultraviolet to near ultraviolet light, to be utilized from the light source.

The micromirror array is operated under control of a computer which provides appropriate microarea address signals to the micromirror array to cause the appropriate micromirrors to be in their "reflect" or "deflect" positions. The appropriate micromirror array pattern for each activation step in each level of amino acids to be added to the peptides is programmed into the computer controller. The computer controller thus controls the sequencing of the images presented by the micromirror array in coordination with the reagents provided to the surface.

The surface may be transparent, allowing the image of the micromirror array to be projected through the surface. The surface may be mounted within a flow cell, with an enclosure sealing off the active surface of the array, allowing the appropriate reagents to be flowed through the flow cell and over the active surface of the array in the appropriate sequence to build up the peptides in the array.

Major Histocompatibility Complex (MHC)

The MHC either class I or class II is expressed across the surface of every nucleated cell of a human being. While MHC class I (MHCI) complexes are present on every nucleated cell, the MHC class II (MHCII) complexes are only present in cells of the immune system (i.e., macrophages and lymphocytes). MHC complexes present peptide fragments of the intracellular contents, allowing the immune system to survey the body for the presence of foreign invaders, as determined by the presentation of non-self peptide sequences. In the case of an autoimmune condition, when the MHC presents a self-peptide, the immune system is stimulated in the same way that the immune system would react to a non-self peptide. Leukocyte antigen genes, including human leukocyte antigen (HLA) genes, that encode the components of the MHC are incredibly diverse, leading to many possible permutations of the MHC, both MHCI and MHCII.

Leukocyte antigen gene sequences, including human leukocyte antigen (HLA) gene sequences, may be found in a number of publicly available databases, including the IPD-IMGT/HLA database (www.ebu.ac.uk/ipd/imgt/hla/) and UNIPROT (www.uniprot.org). Alpha-chains of MHCI complexes of the disclosure may be modified to remove transmembrane, hinge, and/or cytoplasmic regions. To accomplish this modification, a full-length nucleic acid sequence of an α-chain of MHCI complex may be obtained from a public database, edited to remove those sequences encoding a transmembrane, a hinge, and/or a cytoplasmic region, and reverse translated, using, optionally, a codon table optimized for a host T-cell in which the nucleic acid will be expressed (e.g. *E. coli*). Alpha-chains of MHCII complexes of the disclosure may be modified to remove transmembrane and/or cytoplasmic regions. To accomplish this modification, a full-length nucleic acid sequence of an α-chain of MHCII complex may be obtained from a public database, edited to remove those sequences encoding a transmembrane and/or a cytoplasmic region, and reverse translated, using, optionally, a codon table optimized for a host T-cell in which the nucleic acid will be expressed (e.g. *E. coli*). Beta-chains of MHCII complexes of the disclosure may be modified to remove transmembrane and/or cytoplasmic regions. To accomplish this modification, a full-length nucleic acid sequence of a β-chain of MHCII complex may be obtained from a public database, edited to remove those sequences encoding a transmembrane and/or a cytoplasmic region, and reverse translated, using, optionally, a codon table optimized for a host T-cell in which the nucleic acid will be expressed (e.g. *E. coli*).

Peptides and MHC components assemble in the endoplasmic reticulum (ER) of each cell before they are displayed on the cell surface. In vivo, peptides that form complexes with the MHC are by-products of the degradation of cytosolic proteins by the proteasome. Peptides of the disclosure may comprise or consist of any sequence and that sequence may be derived from any polypeptide. For example, peptides of the disclosure may designed by systemically moving one amino acid each step (or, 2, 3, 4, 5, 6, 7, 8, 9, 10, etc) from the N-terminus to the C-terminus of a sequence of a polypeptide in, for example, intervals of between 6 and 30 amino acids (i.e., the length of the peptide intended to be synthesized on the surface of a composition of the disclosure) until the length of the polypeptide has been traversed. Moreover, using the set of peptide sequences generated by moving along the sequence in steps, a further set of peptides may be developed by, for example, substituting the amino acids present in the sequence of each one of those peptides for each one of the possible 20 amino acids to provide all possible sequence variations. In this example, as in Example 1, if the WT1 protein were divided into peptides having 9 amino acids moving one amino acid at each step, the set of peptides provided in FIG. 1 would be generated. If those peptides are then substituted as shown in Example 1, a further set of peptides, a substitution set, may be generated. This process may be applied to any polypeptide to generate at least one peptide or a plurality of peptides of the compositions of the disclosure.

A challenge for identifying points of intervention to either inhibit the immune system or to stimulate the immune system is defining the rules that permit some peptides to be loaded into an MHC while others are not. By using a highly multiplexed format, the compositions and methods of the disclosure provide empirical evidence showing demonstrated ability or inability of a peptide to assemble with MHC I and/or MHCII.

Once a peptide is displayed on the surface of a cell as part of a stable MHC complex, the immune system (e.g. T-cells) samples the peptide-MHC complexes to find sequences that are foreign, or non-self antigens. In autoimmune conditions, the immune system fails to distinguish between self and non-self antigens, ultimately treating cells displaying self-antigens as foreign invaders and attacking healthy tissues. In the same highly multiplexed reaction used to identify immunodominant peptides, the compositions and methods of the disclosure may be used to identify those peptides that stimulate the immune system, including synthetic peptides, modified peptides, and/or neoantigens that may be used to turn a subjects immune system against a cancer cell or to stimulate the immune system to better fight infection. The compositions and methods of the disclosure may be used to validate the power of T-cells comprising a chimeric antigen receptor to identify peptide-MHC complexes on cells that the native immune system would not recognize, including, for example, peptide-MHC complexes on cancer cells.

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the invention.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Embodiments defined by each of these transition terms are within the scope of this invention.

The terms "linked" or "operatively linked" or its equivalents (e.g., "linked operatively") means two or more molecules are positioned with respect to each other such that they are capable of interacting to affect a function attributable to one or both molecules or a combination thereof. A peptide and its corresponding linker may be operatively linked.

The peptides of the disclosure may comprise an epitope of an antibody used to detect the peptide or the peptide-MHC complex. Moreover, antibodies may be contacted to the compositions of the disclosure to determine the epitope of the antibody, including, a naturally occurring antibody. The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

The term "antibody" is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as "analogs") of the antibodies hereof as defined herein. Thus, according to one embodiment hereof, the term "antibody hereof" in its broadest sense also covers such analogs. Generally, in such analogs, one or more amino acid residues may have been replaced, deleted and/or added, compared to the antibodies hereof as defined herein.

Antibodies used to detect peptides and/or peptide-MHC complexes of the disclosure may be raised from any species. In certain embodiments, these antibodies have human CDR sequences even though the framework regions may be from a nonhuman species. In certain embodiments, these antibodies are fully human but may contain one or more modifications such that they are nonnaturally occurring. In certain embodiments, these antibodies are fully human to mimic in vitro, the ability of a human immune system to recognize a peptide and/or peptide-MHC complex of the disclosure bound to the surface of a composition of the disclosure.

Antibody fragments may be incorporated into a detectable agent for recognizing a peptide and/or peptide-MHC complex of the disclosure bound to the surface of a composition of the disclosure. "Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In certain embodiments, a specific binding interaction will discriminate between desirable and undesirable antigens in a sample, in some embodiments more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Nucleic acids of the disclosure may be single-stranded or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a DNA or RNA vector. A vector can be a self-replicating extrachromosomal vector, and preferably, is a DNA plasmid.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the invention. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | G A P I L V F |
|  | Polar - uncharged | C S T M N Q |
|  | Polar - charged | D E K R |
| Aromatic | | H F W Y |
| Other | | N Q D E |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar (hydrophobic) | Aliphatic: | A L I V P |
|  | Aromatic: | F W Y |
|  | Sulfur-containing: | M |
|  | Borderline: | G Y |
| Uncharged-polar | Hydroxyl: | S T Y |
|  | Amides: | N Q |
|  | Sulfhydryl: | C |
|  | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
| --- | --- |
| Ala (A) | Val Leu Ile Met |
| Arg (R) | Lys His |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

All percentages and ratios are calculated by weight unless otherwise indicated.

All percentages and ratios are calculated based on the total composition unless otherwise indicated.

Every maximum numerical limitation given throughout this disclosure includes every lower numerical limitation, as if such lower numerical limitations were expressly written herein. Every minimum numerical limitation given throughout this disclosure will include every higher numerical limitation, as if such higher numerical limitations were expressly written herein. Every numerical range given throughout this disclosure will include every narrower numerical range that falls within such broader numerical range, as if such narrower numerical ranges were all expressly written herein.

The values disclosed herein are not to be understood as being strictly limited to the exact numerical values recited. Instead, unless otherwise specified, each such value is intended to mean both the recited value and a functionally equivalent range surrounding that value. For example, a value disclosed as "20 μm" is intended to mean "about 20 μm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

EXAMPLES

Example 1: HLA Class I Preparation and Array Assembly

Origin of Human Leukocyte Antigen (HLA) and $\beta_2$ Microglobulin (b2m) Proteins:

Cloning and Expression in *E. coli*

HLA-A*02:01 and b2m were provided by Roche Glycart AG (Schlieren, Switzerland) and Roche Diagnostics GmbH (Penzberg, Germany).

HLA-A*11:01, HLA-B*07:02, and HLA-C*07:02 amino acid sequences from UniProt database were truncated to remove the hinge, transmembrane and cytoplasmic regions at the C-terminal end and leader peptide sequence from N-terminal end.

HLA-A*11:01:
(SEQ ID NO: 1)
MGSHSMRYFYTSVSRPGRGEPRFIAVGYVDDTQFVRFDSDAASQRMEPR

APWIEQEGPEYWDQETRNVKAQSQTDRVDLGTLRGYYNQSEDGSHTIQI

MYGCDVGPDGRFLRGYRQDAYDGKDYIALNEDLRSWTAADMAAQITKRK

WEAAHAAEQQRAYLEGRCVEWLRRYLENGKETLQRTDPPKTHMTHHPIS

DHEATLRCWALGFYPAEITLTWQRDGEDQTQDTELVETRPAGDGTFQKW

AAVVVPSGEEQRYTCHVQHEGLPKPLTLRWE

HLA-B*07:02:
(SEQ ID NO: 2)
GSHSMRYFYTSVSRPGRGEPRFISVGYVDDTQFVRFDSDAASPREEPRA

PWIEQEGPEYWDRNTQIYKAQAQTDRESLRNLRGYYNQSEAGSHTLQSM

YGCDVGPDGRLLRGHDQYAYDGKDYIALNEDLRSWTAADTAAQITQRKW

EAAREAEQRRAYLEGECVEWLRRYLENGKDKLERADPPKTHVTHHPISD

HEATLRCWALGFYPAEITLTWQRDGEDQTQDTELVETRPAGDRTFQKWA

AVVVPSGEEQRYTCHVQHEGLPKPLTLRWE

HLA-C*07:02
(SEQ ID NO: 3)
SHSMRYFDTAVSRPGRGEPRFISVGYVDDTQFVRFDSDAASPRGEPRAP

WVEQEGPEYWDRETQKYKRQAQADRVSLRNLRGYYNQSEDGSHTLQRMS

GCDLGPDGRLLRGYDQSAYDGKDYIALNEDLRSWTAADTAAQITQRKLE

AARAAEQLRAYLEGTCVEWLRRYLENGKETLQRAEPPKTHVTHHPLSDH

EATLRCWALGFYPAEITLTWQRDGEDQTQDTELVETRPAGDGTFQKWAA

VVVPSGQEQRYTCHMQHEGLQEPLTLSWE

The amino acid sequences for HLA-A*11:01, HLA-B*07:02, and HLA-C*07:02 proteins were reverse translated to DNA sequences using *E. coli* optimal codon table, synthesized as double stranded DNA, and cloned in plasmid DNA by DNA2.0 (www.dna20.com). Proteins were expressed in *E. coli* in the form of inclusion bodies either by DNA2.0 (HLA-A*11:01) or by Penzberg (HLA-B*07:02 and HLA-C*07:02). Inclusion bodies with expressed proteins were stored at −80° C. before solubilization.

Solubilization of Inclusion Bodies 100 mg of inclusion bodies was transferred in 2.0 ml Eppendorf tube, re-suspended in 1 ml 50 mM Tris-HCl, pH7.8, 5 mM EDTA, 1% Tween 20, 2 mM DTT, and centrifuged at 2,000×g for 2 min. The supernatant was removed and the pellet was loosened by vortexing.

The pellet was mixed with 1 ml 25 mM Tris-HCl, pH7.8, 2M NaCl, 2M urea, 2 mM DTT, and centrifuged at 4,000×g for 2 min. The supernatant was removed and the pellet was loosened by vortexing.

The pellet was mixed with 1 ml 1×PBS, 0.5 mM PMSF and centrifuged at 2,000×g for 2 min. The supernatant was removed and the pellet was loosened by vortexing.

The pellet was dissolved in 1 ml 20 mM Tris-HCl, pH7.8, 8M urea, 100 μM beta-mercaptoethanol, and stored at 4° C. for overnight for complete dissolving. Protein concentration was determined by absorbance at 280 nm assuming 1 A280 unit=1 mg/ml. Purity of the protein was tested with 12% NuPAGE Bis-Tris gel and MES running buffer (Novex) stained with EZblue Staining Reagent (Sigma).

HLA Class I Complex Preparation and Assembly on Array
HLA/b2m Complex Preparation.

Typically, 630 μl of 10 mM Tris-HCl pH8.5 was mixed with 20 μl of 10% BSA in 20 mM Tris-HCl pH 7.8, 300 μg of 30 mg/ml solubilized b2m and 600 μg of 15-40 mg/ml solubilized alpha-chain in the indicated order at room temperature (RT). The control sample contained no b2m protein. Mixed samples were incubated at 4° C. overnight and centrifuged at 12,000×g for 4 min to remove precipitate. The supernatant was concentrated with an AmiconUltra 10K filter (Millipore) using two sample loads of approximately 400 μl and centrifuged at 12,000×g for 2 min each. The sample buffer was replaced with 10 mM Tris pH8.5 by addition of 350 μl 10 mM Tris-HCl pH 8.8 to the filter retained volume and concentrated by centrifugation at 12,000×g for 4 min. The buffer replacement procedure was repeated two more times using 350 μl 10 mM Tris-HCl pH 8.5 each time. After the final centrifuging step, the retained volume (approximately 100 μl) was collected in a fresh tube by centrifugation at 1,000×g for 2 min, filtered through 5.0 μm Ultrafree filter (Millipore) and stored at 4° C.

HLA Class I On-Array Complex Assembly and Detection.

Peptide array slides, after synthesis and deprotection, were stored at −20° C. in a sealed container or used immediately. Before sample application, the slides were incubated in 1× Binding Buffer (1% casein, 10 mM Tris pH7.4, 0.25% Tween 20) with 0.7 μg/ml Cy-5 labeled streptavidin (Amersham) for array blocking and fiducials staining for 1 h at RT, rinsed in water, and dried by a 30 second centrifugation using a table-top centrifuge equipped with a slide holder.

The prepared HLA class I samples were loaded in incubation chambers attached to the surface of peptide arrays without any additional treatment or dilution. After incubation at RT overnight, incubation chambers were removed, arrays were rinsed in water, and the HLA complexes were stained for 1 h at RT with an anti-HLA-A,B,C conformational antibody (Alexa647-MEM123 (Novus) 300-fold diluted in 1× Binding Buffer). After staining, the arrays were rinsed in water, dried, and scanned at 635 nm.

Parameters Affecting On-Array Peptide/HLA Complex Assembly:

Influential Parameters for Successful Peptide/HLA/b2m Assembly:

With respect to the present example, the optimal concentration of BSA was found to be 2-3% added to HLA/b2m mixture. No complex formation was observed without BSA.

With respect to the present example, the optimal HLA to b2m mole/mole ratio for complex preparation was found between 1:1 and 1:2.

In the process of HLA/b2m mixture preparation, HLA-B*07:02 and HLA-C*07:02 proteins formed a precipitate during dilution from 8M urea stock. This effect is pH dependent and can be minimized by using 10 mM Tris-HCl, pH8.5 buffer.

Complex assembly intensity signal is proportional to HLA/b2m concentration. For optimal concentration, two factors should be considered: first, increasing HLA/b2m concentration increases both specific and non-specific signal (background); and, second, HLA alleles have varying dependence of signal on HLA/b2m concentration. That means that an optimal concentration should be independently found for each allele. Conditions described in "HLA/b2m complex preparation" section may be used as a template for optimization.

At least overnight incubation is recommended for both steps: HLA/b2m complex preparation and peptide/HLA/b2m complex assembly on array.

To optimize the linker for peptide attachment to the slide surface, three different linkers, hexanoic acid, PEG and G/S amino acid mix at 3:1 ratio, were tested at five different lengths from 1 to 5. Linker consisting of three hexanoic acid molecules was found optimal using signal/background ratio as a metric. Furthermore, particularly if the surface has a net positive charge, the linker may be optimized to include at least one negative monomer. For example the linker may include at least one negatively-charged amino acid.

Conformational antibodies detecting HLA/b2m complex, Cy5-labeled W6/32 (NBP2-00439) or Alexa 647-labeled MEM123 (NB500-505AF647) both from Novus Biological can be used for detection of HLA/b2m assembled on peptide array at optimal antibody dilution factor of 1:100 and 1:300, respectively.

Parameters that have Minimal or Negative Effect on Peptide/HLA/b2m Assembly:

Several reagents were reported as important for efficient peptide/HLA/b2m complex assembly in literature. Among them are 0.4M L-arginine, 0.25% glucopyranoside, 5 mM L-glutathione reduced/0.5 mM L-glutathione oxidized, auxiliary peptides such L-GL dipeptide and low affinity peptides. These reagents were found to either have minimal effect or to have an inhibitory effect on HLA/b2m complex assembly on peptide array.

Other parameters including pH in range from 5.5 to 8.5, 20 mM to 1M NaCl or KCl, 1 mM $MgCl_2$ or $CaCl_2$, 0.1% casein, 60 mM urea were tested and found to either have minimal effect or to have an inhibitory effect on HLA/b2m complex assembly on peptide array.

Several other antibodies were tested for detection of assembled HLA/b2m complexes: anti-b2m, anti-HLA MEM81, MEM147, and BB7.2. All these antibodies showed either low signal or high background compared to w6/32 and MEM123 antibody, except BB7.2, which showed good signal/background ratio, but was not used in this study because of its HLA-A restriction and inability to detect HLA-B and HLA-C alleles.

Example 2: MHCI Surface Array Design

Set 1

12-Plex Layout

Batched 9Mer Peptides (123,675 Peptides):

9-mer peptides tiled at 1 amino acid step size to represent 5 control proteins; NY-ES01, WT1, MAGE3, MAGE4, FOXP3; 3 different linker types (PEG8, 6-amino hexanoic acid, Gly:SER 4:1 mix), and 5 different linker lengths.

TABLE 1

| UNIPROT ID | Protein Length | Name | Linker Type | Linker Length | Replicates | Total |
|---|---|---|---|---|---|---|
| P78358 | 180 | NY-ES01 | 3 | 5 | 5 | 13555 |
| P19544 | 449 | WT1 | 3 | 5 | 5 | 33675 |
| P43358 | 317 | MAGE4 | 3 | 5 | 5 | 23775 |
| P43357 | 314 | MAGE3 | 3 | 5 | 5 | 23550 |
| Q9BZS1 | 431 | FOXP3 | 3 | 5 | 5 | 32325 |

Initial experimental design to optimize pMHC formation and detection involved 5 known cancer proteins, 3 different peptide linker types, and five different linker lengths (1-5 repeats/monomers).

Set 2

12-plex layout: Two peptides from Wilms' Tumor and one other peptide. Also known as nephroblastoma, Wilms' tumor is a rare kidney cancer.

Single Amino-Acid Substitution Analysis (40,500 Peptides):

3 well-studied control peptides for which the corresponding antibody is available and can recognize peptide bound to MHCI are synthesized. The antibodies have nanomolar binding affinities and therefore, it is expected that the antibodies will specifically bind to the peptide-MI-ICI complex. For each position in the 9-mer peptide, 20 peptides will be synthesized by substituting all 20 amino acids. For a 9mer, 20*9=180 peptides are needed to perform a full single amino acid substitution analysis. 3 different peptide linker types (PEG8, 6-amino hexanoic acid, Gly:SER 4:1 mix) and 5 different linker lengths (linker length is defined as number of synthesis cycles for each linker monomer, 1/2/3/4/5) are also included. Every peptide is tested with each linker type and length in 5 replicates.

Variables under Optimization for Sets 1 and 2

TABLE 2

| Off/On Array MHC-I complex formation | Purification of proteins from inclusion bodies | Degraded and aggregated products |
|---|---|---|
| | Assembly of complex | Optimal buffer (including pH) Auxiliary peptide (including type, concentration, affinity) Arginine |
| | Purification of assembled complex for long-term storage | |
| | Binding of assembled complex on-array | Binding conditions, buffer, wash |
| | Effect of linker(s) on complex binding | |
| Detection of MHC-I complex | Increase signal to noise | |
| Detection of antibody detected peptide/pMHCI complex | | |
| Validation of array detected peptide/pMHCI complex | | |
| Detection of TCR/pMHC complex | | |
| Optimization for HLA allotypes | | |
| Identification of high-affinity peptide for disease-specific TCR from proteome | | |

For both Sets 1 and 2, the pMHC complex formation on surface was successful.

Figure 1B:
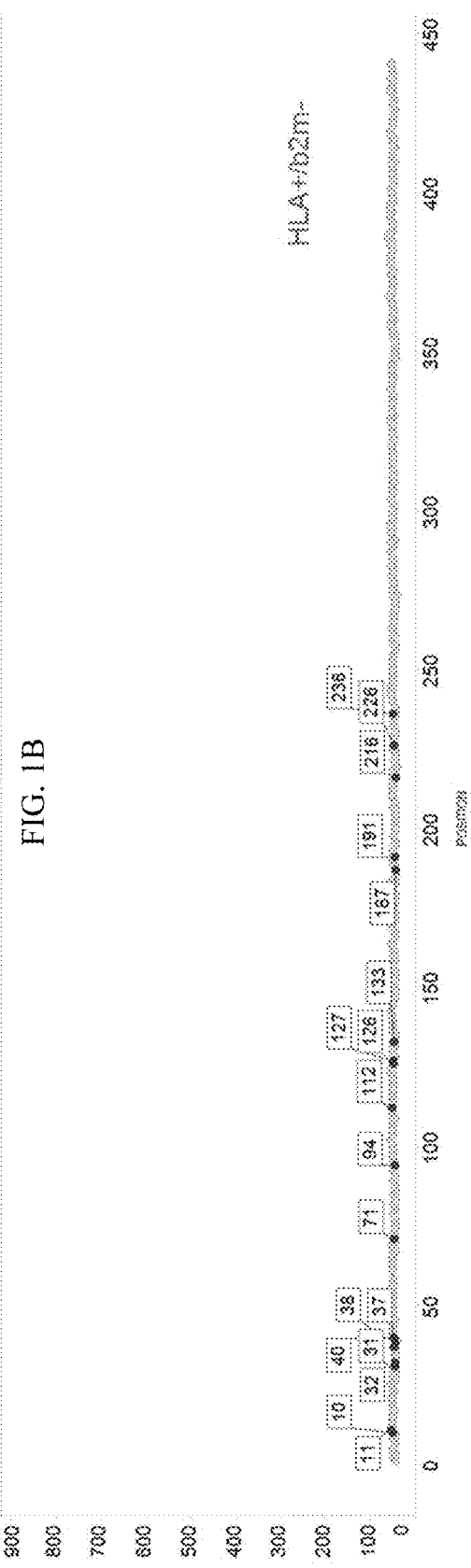

With respect to Set 1, antibody W6/32 (Novus Biosciences) labeled with pCy5 was added to the surface to bind to any properly assembled pMHC complex. On the top panel of FIG. 1, each peak is a separate pMHC complex. Some complexes have been reported in the literature while others have not. Most complexes have a leucine at the second position (positions 2 and 8 are considered to be anchor positions). FIG. 1 (bottom panel) is HLA alpha subunit only (no "b2m" or beta subunit) negative control.

Example 3: Identification of Immunodominant
Peptides and Comparison to NetMHC 3.4

Compositions and methods of the disclosure may be used to identify those peptides that would be immunodominant when presented by an MHC in vivo. Because the compositions of the disclosure can comprise at least $10^6$ unique peptides to the surface simultaneously, any antigen of interest may be presented in, for example, every permutation of a 9 amino acid sequence bound to an MHCI complex on the surface. In a single, highly-multiplexed experiment, using any antibody that specifically recognizes fully and properly assembled peptide-MHCI complexes, those peptides that could be presented in vivo are easily identified. In the same experiment, one or more T-cells may be introduced to the surface to determine which of the peptides contained in properly assembled peptide-MHCI complex stimulate one or more of the T-cells. Based on these two criteria alone (that the peptide forms a proper peptide-MHC complex and stimulates a T-cell), both of which may be determined in a single experiment for at least $10^6$ unique peptides, the compositions and methods of the disclosure provide a superior means for identifying in vitro those peptides that would be immunodominant if they were presented by an MHC in vivo.

The power of the compositions and methods of the disclosure was compared to the power of a computer algorithm for predicting immunodominant peptides, NetMHC 3.4, which is the current industry standard method.

Figure 2:
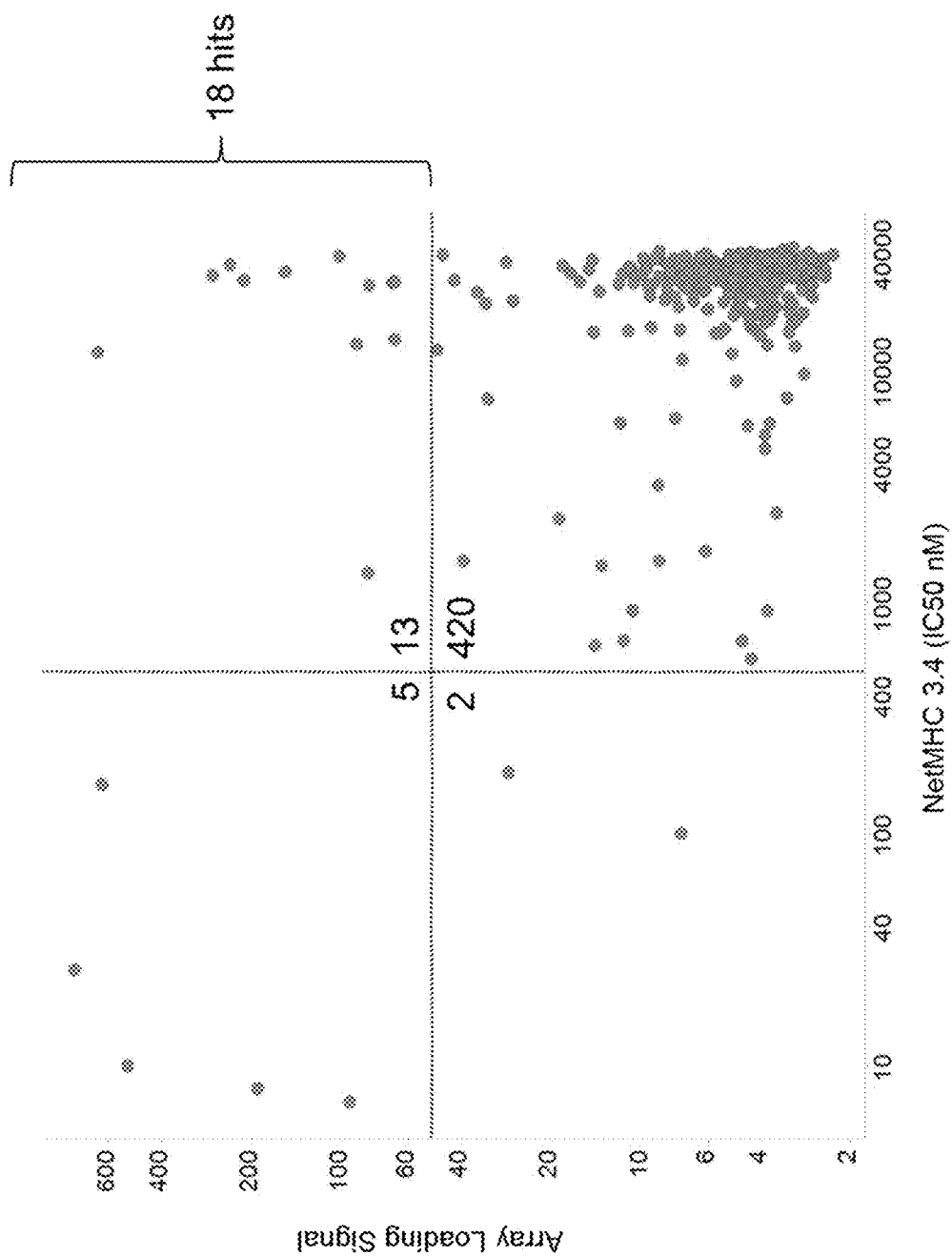
FIG. 2 a plot depicting a plurality of WT1 peptides, each 9 amino acids in length and each having a unique sequence along the wild type sequence of the WT1 protein, organized into quadrants based on either their signal intensity when bound to MHCI on a surface of the disclosure and detected by a labeled antibody, or their predicted binding affinity, as estimated by NetMHC 3.4 (an algorithm that is widely used in the field for identifying peptide antigens). Any antibody that specifically recognizes fully assembled MHCI complexes may be used to identify those peptides that would be presented by an MHCI in vivo. This analysis was performed and the results were compared to the predicted peptides identified by and compared to the peptides predicted by NetMHC 3.4 to form complexes with MHCI. Of the 440 peptides plotted, NetMHC 3.4 identified 433 peptides as having an affinity too low to bind MHCI, and, in contrast, identified only seven peptides as having a theoretical capacity to bind MHCI. In sharp contrast, the compositions and methods of the disclosure identified 18 peptides that actually bind MHCI, including 13 peptides (the upper right quadrant) that the NetMHC 3.4 algorithm would have discarded.

FIG. 2 provides a plot depicting a plurality of WT1 peptides, each 9 amino acids in length and each having a unique sequence along the wild type sequence of the WT1 protein, organized into quadrants based on either their signal intensity when bound to MHCI on a surface of the disclosure and detected by a labeled antibody, or their predicted binding affinity, as estimated by NetMHC 3.4. Any antibody that specifically recognizes fully assembled MHCI complexes may be used to identify those peptides that would be presented by an MHC in vivo.

Of the 440 peptides plotted, NetMHC 3.4 identified 433 peptides as having an affinity too low to bind MHCI, and, in contrast, identified only seven peptides as having a theoretical capacity to bind MHCI. In sharp contrast, the compositions and methods of the disclosure identified 18 peptides that actually bind MHCI, including 13 peptides (the upper right quadrant) that the NetMHC 3.4 algorithm would have discarded.

Figure 3:
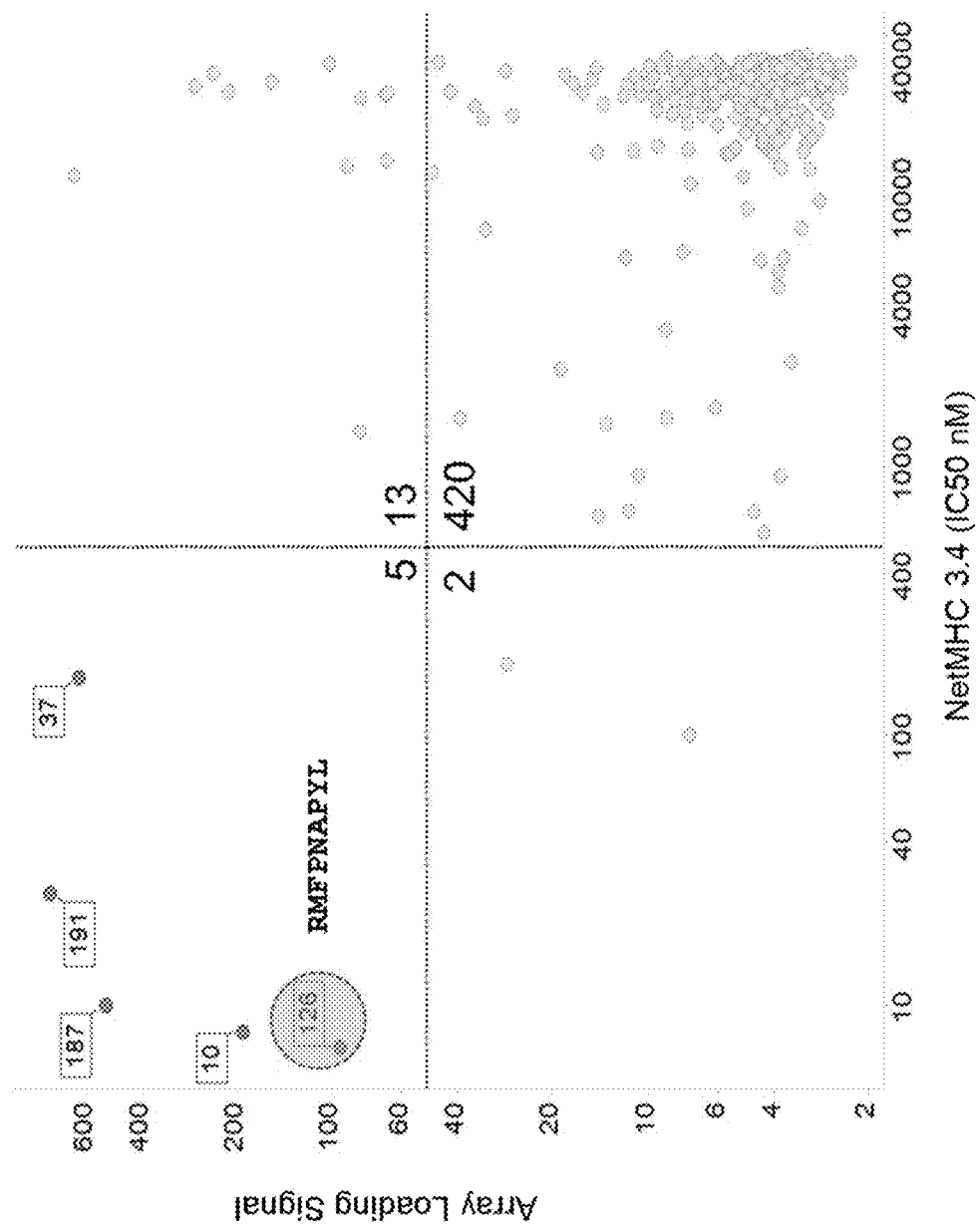
FIG. 3 is the same plot shown in FIG. 2, with particular emphasis on the upper left quadrant. This quadrant represents those peptides with demonstrated binding capacity to MHCI according to the compositions and methods of the disclosure that, when analyzed using the current industry standard method of identifying immunodominant peptides, NetMHC, would have been predicted by the algorithm to bind MHCI with sufficient affinity. Of particular interest is the highlighted peptide, referred to herein, as WT1 peptide126 (having amino acid sequence RMFPNAPYL (SEQ ID NO: 7)).

FIG. 3 highlights the upper left quadrant. The upper left quadrant represents those peptides with demonstrated binding capacity to MHCI according to the compositions and methods of the disclosure that, when analyzed using the current industry standard method of identifying immunodominant peptides, NetMHC, would have been predicted by the algorithm to bind MHCI with sufficient affinity. Of particular interest is the highlighted peptide, referred to herein, as WT1 peptide 126.

Figure 4:
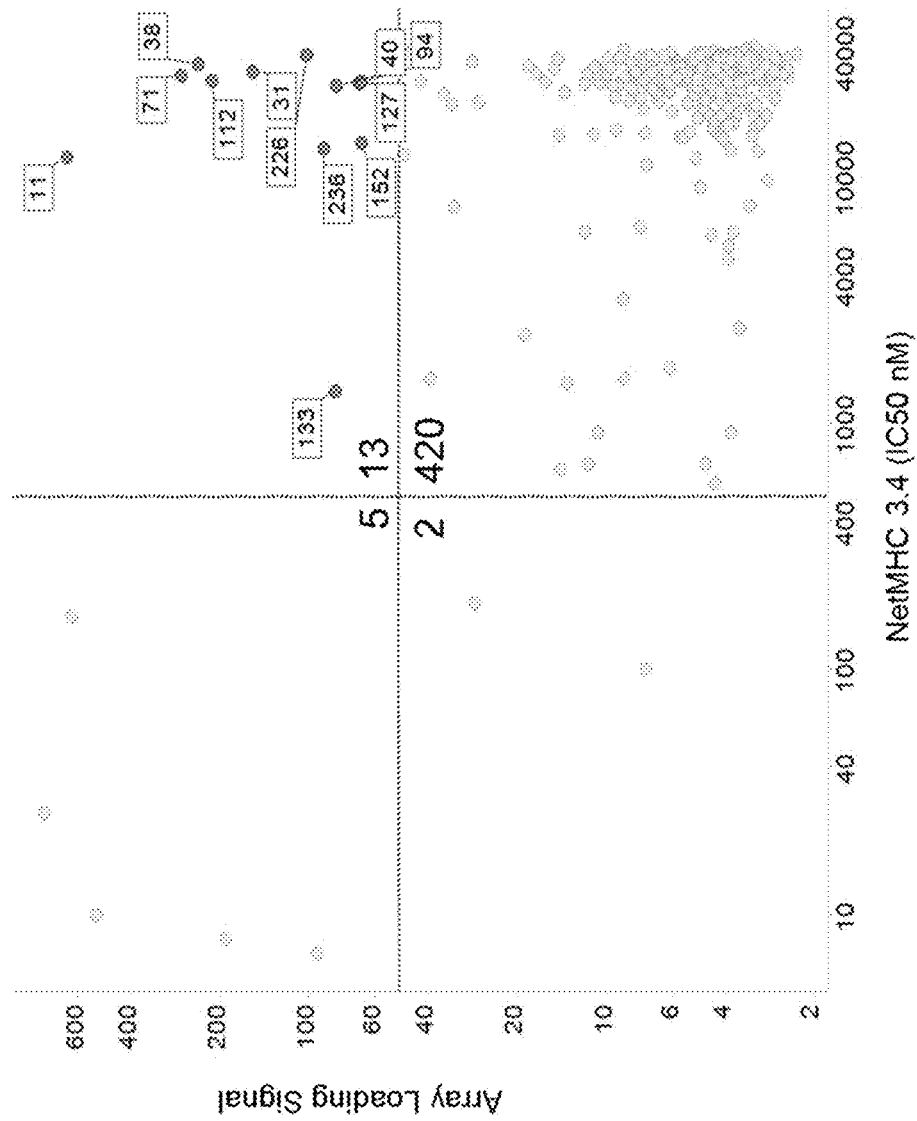
FIG. 4 is the same plot shown in FIG. 2, with particular emphasis on the upper right quadrant. This quadrant represents those peptides with demonstrated binding capacity to MHCI according to the compositions and methods of the disclosure that, when analyzed using the current industry standard method of identifying immunodominant peptides, NetMHC, would have been discarded by the algorithm as being theoretically incapable of binding MHCI with sufficient affinity. In other words, the compositions and methods of the disclosure empirically validated 13 peptides that, when analyzed using the NetMHC program alone, would have been false negatives.

FIG. 4 highlights the upper right quadrant. The upper right quadrant represents those peptides with demonstrated binding capacity to MHCI according to the compositions and methods of the disclosure that, when analyzed using the current industry standard method of identifying immunodominant peptides, NetMHC, would have been discarded by the algorithm as being theoretically incapable of binding MHCI with sufficient affinity. In other words, the compositions and methods of the disclosure empirically validated 13 peptides that, when analyzed using the NetMHC program alone, would have been false negatives.

Figure 5:
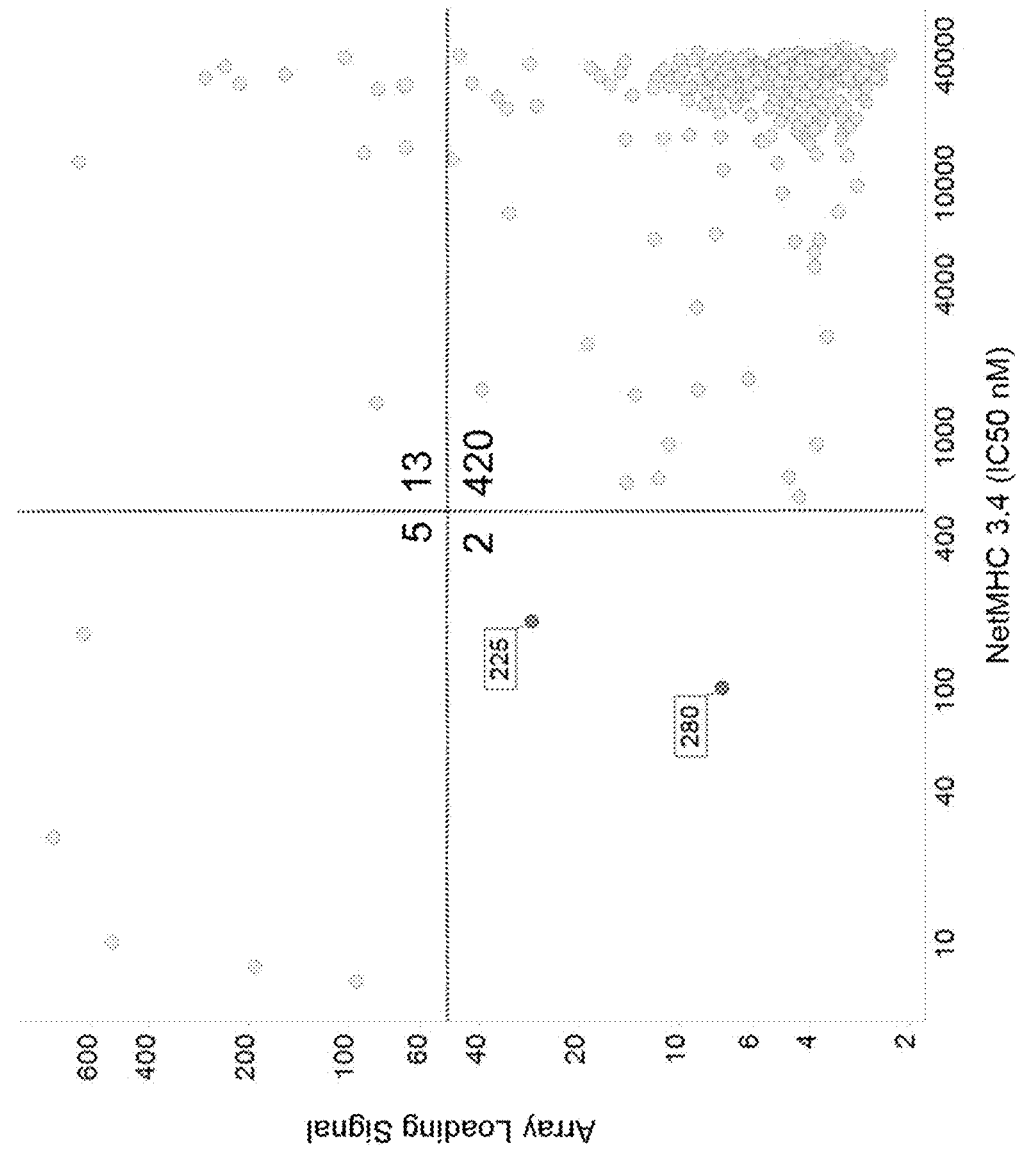
FIG. 5 is the same plot shown in FIG. 2, with particular emphasis on the lower left quadrant. This quadrant represents those peptides that, when analyzed using the current industry standard method of identifying immunodominant peptides, NetMHC, would have been predicted to bind MHCI with sufficient affinity, but when tested using the compositions and methods of the disclosure, were shown empirically not to form fully assembled peptide-MHCI complexes. In other words, the compositions and methods of the disclosure empirically identified 2 peptides that, when analyzed using the NetMHC program alone, would have been false positives.

FIG. 5 highlights the lower left quadrant. The lower left quadrant represents those peptides that, when analyzed using the current industry standard method of identifying immunodominant peptides, NetMHC, would have been predicted to bind MHCI with sufficient affinity, but when tested using the compositions and methods of the disclosure, were shown empirically not to form fully assembled peptide-MHCI complexes. In other words, the compositions and methods of the disclosure empirically identified 2 peptides that, when analyzed using the NetMHC program alone, would have been false positives.

Because of the diversity of MHC components and the nearly infinite possible sequences for peptides to form complexes with the MHC, there is a long-felt and unmet need for a highly multiplexed system that can recapitulate the environment of the ER and empirically and rapidly determine which MHC components can form complexes with the vast array of peptides available, and, subsequently, which of those peptide-MHC complexes stimulate the immune system (e.g. T-cells).

Computer modeling of this complex system has been insufficient because, as shown in this disclosure, many peptide-MHC complexes that actually form are not predicted to assemble using existing algorithms. Conversely, some of the peptide-MHC complexes predicted to assemble have been shown by the studies presented in this disclosure to form unstable complexes.

Figure 7:
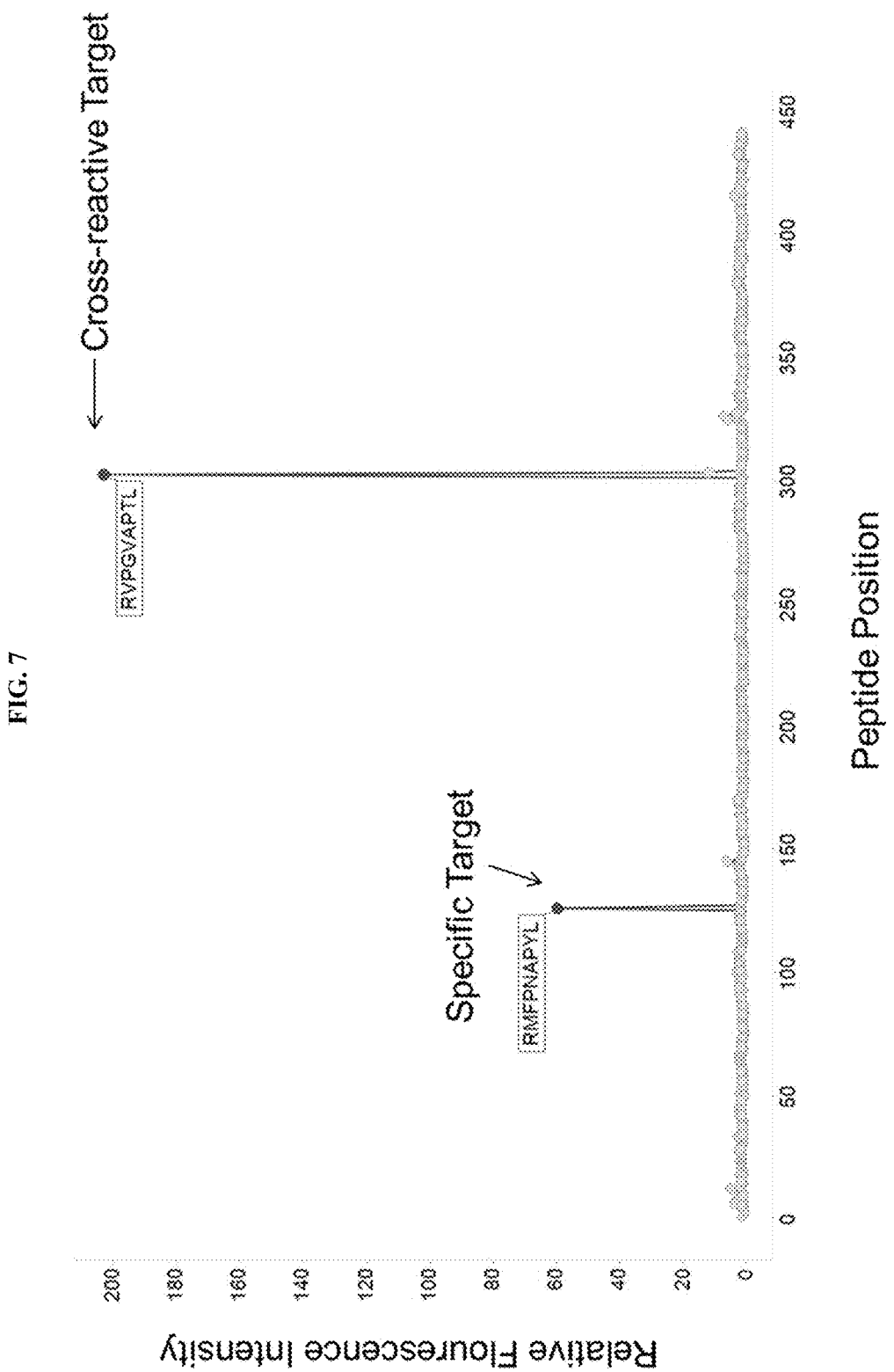
FIG. 7 is a plot depicting the ESK1 antibody binding specificity to peptide-MHC assemblies for WT1 9mer peptides. The data show the relative fluorescence intensities for the specific target (RMFPNAPYL (SEQ ID NO: 7)) and the cross-reactive target (RVPGVAPTL (SEQ ID NO: 9)).
Figure 8:
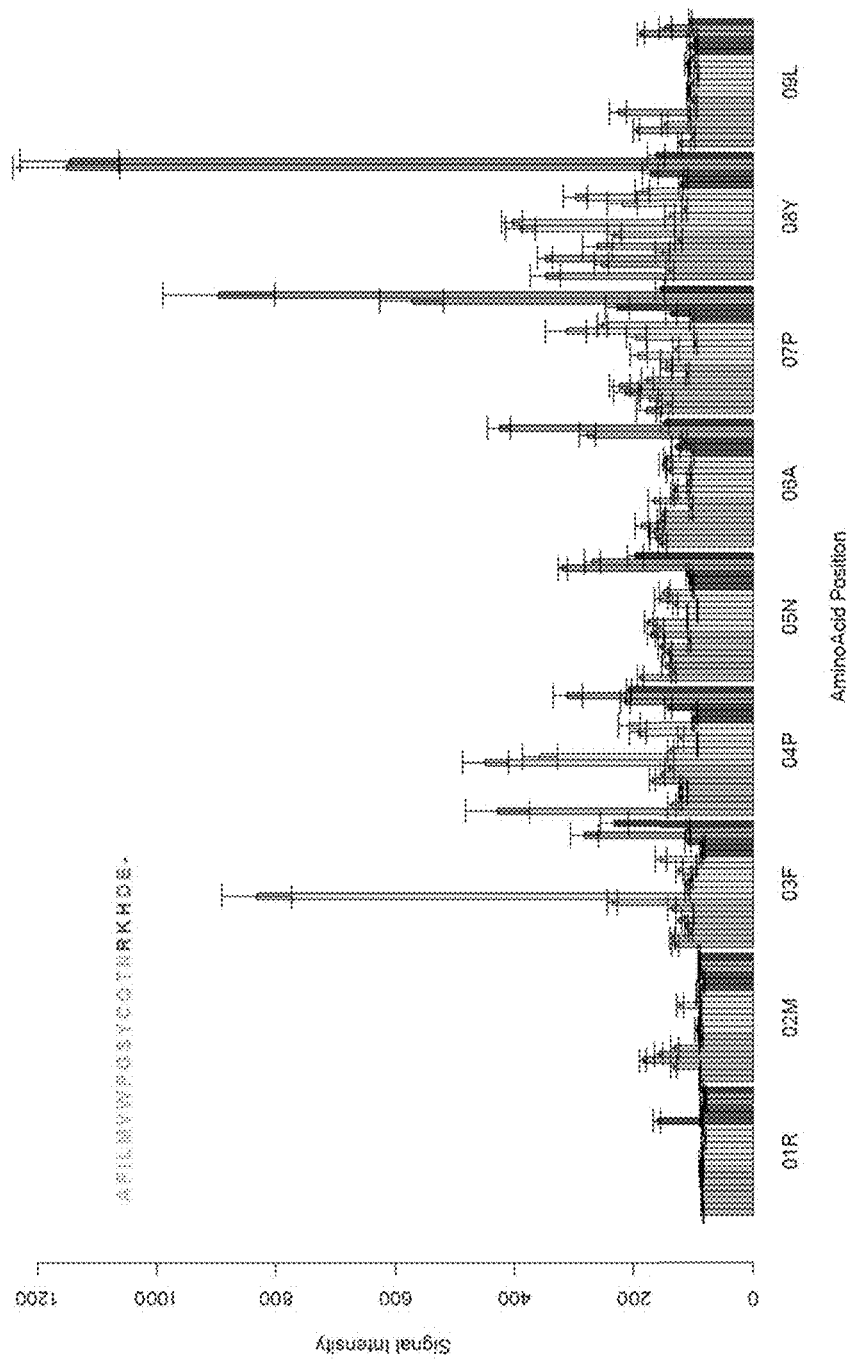
FIG. 8 is a plot depicting the ESK1 antibody binding specificity for "RMFPNAPYL" (SEQ ID NO: 7) variants. Each amino acid of the 9 amino acid peptide was substituted for each of the 20 possible amino acids to identify those positions within this peptide that are essential for forming a proper peptide-MHCI complex. The figure shows all 20 amino acids in a line by their single amino acid letter codes, grouped by characteristics: AFILMVWPGSYCQTNRKHDE. The amino acids A, F, I, L, M, V, W and P are nonpolar amino acids. The amino acids G, S, Y, C, Q, T, N are polar amino acids. The amino acids R, K and H are basic amino acids. The amino acids D and E are acidic amino acids.

To further demonstrate the power of the highly multiplexed and empirically-based methods of the disclosure, FIGS. 7 and 8 provides a sequence analysis of "RMFPNAPYL" (SEQ ID NO: 7) variants to which the ESK1 may bind with varying affinities. Because the array of peptides on the surface is spatially-ordered, the sequence of every peptide is immediately known. Each amino acid of the 9 amino acid peptide was substituted for each of the 20 possible amino acids to identify those positions within this peptide that are essential for forming a proper peptide-MHCI complex. FIG. 8 shows all 20 amino acids in a line by their single amino acid letter codes, grouped by characteristics: AFILMVWPGSYCQTNRKHDE. The amino acids A, F, I, L, M, V, W and P are nonpolar amino acids. The amino acids G, S, Y, C, Q, T, N are polar amino acids. The amino acids R, K and H are basic amino acids. The amino acids D and E are acidic amino acids.

Example 4: Linkers with Negatively-Charted
Monomers

Previously a number of linkers were evaluated for peptide attachment to the array surface to optimized peptide-MHC assembly on surfaces of the assembly. From that study, a linker consisting of three to five HEX moieties (each moiety comprising 6-amino hexanoic acid) was selected as a preferred linker based upon the criteria of highest signal and low background after pMHC complex detection with HLA specific antibodies.

Continuing studies have involved array experiments with well-characterized HLA2-specific peptides that are not only as strong HLA2 binders, but also as biologically relevant peptides with a strong immunogenic effect. Using 15 of these peptides as a positive 'gold standard' control, it was discovered that only 7 of these peptides showed pMHC complex formation on a surface of the disclosure using the preferred HEX linker.

Analysis of substitution plots that depict the effect of all 20 amino acid and the deletion at each position of control peptides on pMHC formation revealed a preference of negatively charged amino acids, aspartate (D) and glutamate (E), at multiple positions for some of the 7 HLA2 binding peptides. While not wishing to be bound by theory, the surface may have an excess of positive charge and the preferred negative charge on the peptides may play a charge compensatory role.

To investigate the effect of charge, different linkers with both negative and positive charges that are listed below were introduced into the compositions of the disclosure:
1. Surface-5HEX-peptide
2. Surface-HEX-E-3HEX-peptide
3. Surface-HEX-D-3HEX-peptide
4. Surface-HEX-K-3HEX-peptide
5. Surface-2HEX-E-HEX-peptide
6. Surface-3HEX-GluB-peptide (GluB=t-butyl protected Glutamic acid linked through the side-chain)

Linker 1 contains 5 hexanoic (HEX) moieties. Linkers 2-4 have a negatively charged moiety glutamate (E), or aspartate (D), or a positively charged lysine (K), respectively, separated from the peptide by three HEX moieties. Linker 5 is similar to linker 2, but has only one HEX between E and the peptide. Linker 6 is another negatively charged linker that has three HEX moieties connected to the side chain of amino acid analog GluB with free carboxyl group carrying a negative charge.

Analysis of peptide-MHC assembly formation for 15 control peptides showed improved binding for peptides attached with negative charged linkers that allowed detection of 11 peptides compared to 7 peptides detected with HEX only linker. The improvement was less noticeable for Linker 6 with GluB amino acid. In contrast, use of positively charged Linker 4 reduced the number of detectable peptides from 7 to 5.

FIGS. 10A and 10B demonstrate the increased signal intensity observed from peptide-MHC assemblies when a linker is used that incorporates at least one negatively-charged monomer, which in this case is an aspartate (D). The linker tested in FIG. 10B corresponds to linker 3 above.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

Other Embodiments

While particular embodiments of the disclosure have been illustrated and described, various other changes and modifications can be made without departing from the spirit and scope of the disclosure. The scope of the appended claims includes all such changes and modifications that are within the scope of this disclosure.

---

What is claimed is:

1. A peptide microarray comprising a plurality of peptides, wherein the peptides form a plurality of peptide-major histocompatibility complex (peptide-MHC) assemblies, each assembly comprising a microarray peptide and a major histocompatibility complex (MHC),
   wherein:
   the peptide is an integral component of the MHC and is attached to a surface of the peptide microarray at its C-terminus through a linker;
   the MHC is a class I MHC comprising an α-chain and a β2-microglobulin (β2m),
   wherein the α-chain of the MHC is encoded by a sequence derived from a human leukocyte antigen (HLA) selected from the group consisting of an HLA-A gene, an HLA-B gene, an HLA-C gene, an HLA-E gene, an HLA-F gene, an HLA-G gene, an HLA-K pseudogene and an HLA-L pseudogene;
   the plurality of peptides is spatially ordered and their sequences are predetermined; and
   the plurality of peptides are synthesized on the surface.

2. The peptide microarray of claim 1, wherein the MHC comprises a carrier molecule.

3. The peptide microarray of claim 2, wherein the carrier molecule is bovine serum albumin (BSA).

4. The peptide microarray of claim 1, wherein the linker comprises hexanoic acid.

5. The peptide microarray of claim 1, wherein the linker comprises polyethylene glycol (PEG).

6. The peptide microarray of claim 1, wherein the linker comprises a mixture of Glycine (G) and Serine (S) amino acids.

7. The peptide microarray claim 1, wherein the linker comprises between 1 and 5 monomer units.

8. The peptide microarray of claim 1, wherein the linker comprises at least one negatively-charged monomer unit.

9. The peptide microarray of claim 1, wherein the α-chain of the MHC is truncated to remove the hinge, transmembrane and cytoplasmic regions at the C-terminal end.

10. The peptide microarray of claim 1, wherein the α-chain is encoded by a sequence derived from an HLA gene selected from the group consisting of an HLA-A gene, an HLA-B gene, and an HLA-C gene.

11. The peptide microarray of claim 1, wherein each microarray peptide of each assembly comprises between 6 and 30 amino acids, inclusive of the endpoints.

12. The peptide microarray of claim 1, wherein the plurality of peptides are synthesized in situ using a digital micromirror device (DMD), wherein the DMD comprises at least one micromirror, wherein each micromirror corresponds to a microarea of the surface and wherein the micromirror corresponding to the microarea directs the synthesis of each peptide in the microarea.

13. The peptide microarray of claim 12, wherein a first microarea comprises at least a first peptide having a unique amino acid sequence when compared to the amino acid sequence of at least a second or subsequent peptide within each second or subsequent microarea.

14. The peptide microarray of claim 13, wherein the first microarea comprising at least one peptide having a unique amino acid sequence further comprises at least one replicate of the peptide having a unique amino acid sequence.

15. The peptide microarray of claim 13 or 14, wherein the first microarea comprises at least a first peptide having a unique amino acid sequence when compared to the amino acid sequence of at least a second or subsequent peptide within each second or subsequent microarea on the surface.

16. The peptide microarray of claim 1, wherein the surface comprises $1.24 \times 10^{13}$ peptides per square centimeter.

17. The peptide microarray of claim 1, further comprising at least one T-cell.

18. The peptide microarray of claim 17, further comprising a detectable agent that recognizes a molecule released from the at least one T-cell upon activation of the at least one T-cell by at least one peptide on the surface.

19. The peptide microarray of claim 1, wherein peptide microarray comprises at least 2 surfaces.

20. The peptide microarray of claim 1, wherein the plurality of peptides comprises at least 1,000,000 unique peptide sequences.

21. The peptide microarray of claim 20, wherein the plurality of peptides comprises up to 2,900,000 unique peptide sequences.

22. The peptide microarray of claim 1, wherein the peptide and the MHC are bound by a non-covalent interaction to form the peptide-MHC assembly.

23. The peptide microarray of claim 10, wherein the α-chain is encoded by a sequence derived from the HLA-A*11:01, HLA-B*07:02, or HLA-C*07:02 amino acid sequences from the UniProt database, which are truncated to remove the hinge, transmembrane and cytoplasmic regions at the C-terminal end and leader peptide sequence from N-terminal end.

* * * * *